US008492552B2

(12) United States Patent
Ying et al.

(10) Patent No.: US 8,492,552 B2
(45) Date of Patent: Jul. 23, 2013

(54) N-HETEROCYCLIC CARBENE METALLACYCLE CATALYSTS AND METHODS

(75) Inventors: Jackie Y. Ying, Singapore (SG); Eric Assen B. Kantchev, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 313 days.

(21) Appl. No.: 12/452,204

(22) PCT Filed: Jun. 20, 2007

(86) PCT No.: PCT/US2007/014393
§ 371 (c)(1),
(2), (4) Date: Apr. 2, 2010

(87) PCT Pub. No.: WO2008/156451
PCT Pub. Date: Dec. 24, 2008

(65) Prior Publication Data
US 2010/0197920 A1 Aug. 5, 2010

(51) Int. Cl.
*C07F 15/00* (2006.01)
*B01J 31/12* (2006.01)

(52) U.S. Cl.
USPC .................. 548/103; 502/155; 252/182.33

(58) Field of Classification Search
USPC .................. 502/155; 548/103; 252/182.33
See application file for complete search history.

(56) References Cited

U.S. PATENT DOCUMENTS

| | | | |
|---|---|---|---|
| 5,312,940 A | 5/1994 | Grubbs et al. |
| 5,405,924 A | 4/1995 | Kelsey |
| 5,977,393 A | 11/1999 | Grubbs et al. |
| 6,060,568 A | 5/2000 | Cavell et al. |
| 6,225,488 B1 | 5/2001 | Mukerjee et al. |
| 6,342,621 B1 | 1/2002 | Mukerjee et al. |
| 6,492,525 B1 | 12/2002 | Bertrand et al. |
| 2002/0013473 A1 | 1/2002 | Grubbs et al. |
| 2002/0156295 A1 | 10/2002 | Buchwald |
| 2002/0198423 A1 | 12/2002 | Nolan et al. |
| 2003/0100119 A1 | 5/2003 | Weinberge et al. |
| 2003/0100776 A1 | 5/2003 | Grubbs et al. |
| 2004/0210055 A1 | 10/2004 | Nolan et al. |
| 2005/0043541 A1 | 2/2005 | Walter et al. |
| 2005/0261451 A1 | 11/2005 | Ung et al. |
| 2006/0004158 A1 | 1/2006 | Moszner et al. |
| 2006/0122398 A1 | 6/2006 | Karch et al. |
| 2006/0173186 A1 | 8/2006 | Buchwald et al. |
| 2006/0287544 A1 | 12/2006 | Amoroso et al. |
| 2007/0004917 A1 | 1/2007 | Bertrand et al. |
| 2007/0073055 A1 | 3/2007 | Organ et al. |
| 2007/0088166 A1 | 4/2007 | Zhang |

FOREIGN PATENT DOCUMENTS

| | | |
|---|---|---|
| GB | 2376946 A | 12/2002 |
| WO | WO 2005/030782 A2 | 4/2005 |
| WO | WO 2008/156451 A1 | 12/2008 |

OTHER PUBLICATIONS

Cao, X-H et al.: Synthesis and crystal structure of [1,3-N,N-bis{2,6-diisopropylphenyl}imidazol-2-ylidene]chloro-[N,N-dimethylbenzylamine-2-C,N]palladium(II). J. of Coord. Chem., vol. 60, pp. 207-211, 2007.*
Invitation to Pay Additional Fees for PCT/US2007/014393 mailed Feb. 25, 2008.
International Search Report and Written Opinion for PCT/US2007/014393 mailed May 23, 2008.
International Preliminary Report on Patentability for PCT/US2007/014393 mailed Oct. 13, 2008.
Ackermann, General and efficient indole syntheses based on catalytic amination reactions. Org Lett. Feb. 3, 2005;7(3):439-42.
Ackermann, General and efficient indole syntheses based on catalytic amination reactions. Org Lett. Feb. 3, 2005;7(3):439-42. Supporting Information.
Anderson et al., General Catalysts for the Suzuki-Miyaura and Sonogashira Coupling Reactions of Aryl Chlorides and for the Coupling of Challenging Substrate Combinations in Water. Angew Chem Int Ed Engl. Sep. 26, 2005;44(38):6173-7.
Andrus et al., Palladium—Imidazolium Carbene Catalyzed Aryl, Vinyl, and Alkyl Suzuki-Miyaura Cross Coupling. Org Lett. Nov. 15, 2001;3(23):3761-4.
Arduengo III et al., A Stable Crystalline Carbene. J Am Chem Soc. 1991;113(1):361-363.
Arduengo III et al., Imidazolylidenes, imidazolinylidenes and imidazolidinesm. Tetrahedron. 1999;55:14523-14534.
Barder et al., Catalysts for Suzuki-Miyaura Coupling Processes: Scope and Studies of the Effect of Ligand Structure. J Am Chem Soc. Apr. 6, 2005;127(13):4685-96.
Bartolomé et al., Neutral Organometallic Palladium(II) Aquo Complexes. Organometallics. Jul. 2002;21(17):3536-3543.
Bourissou et al., Stable Carbenes, Chem. Rev. 2000, 100, 39-92.
Calimsiz et al., Pd-PEPPSI-IPent: low-temperature negishi cross-coupling for the preparation of highly functionalized, tetra-ortho-substituted biaryls. Angew Chem Int Ed Engl. Mar. 8, 2010;49(11):2014-7.
Campeau et al., High-Yielding Intramolecular Direct Arylation Reactions with Aryl Chlorides, Org. Lett. 2005, 7(9), 1857-1860.

(Continued)

Primary Examiner — Charanjit Aulakh
(74) Attorney, Agent, or Firm — Wolf, Greenfield & Sacks, P.C.

(57) ABSTRACT

The present invention generally relates to materials and methods for catalytic reactions, including transition metal-catalyzed cross-coupling reactions. The materials may be stable metal complexes that do not require special handling or processing conditions. In some cases, materials of the invention advantageously may be synthesized in one synthetic step without the need for isolation of intermediate compounds. Also, materials of the invention may be synthesized from inexpensive and readily available starting materials, under relatively mild reaction conditions that do not require the exclusion of air, water, and the like. In some embodiments, the material is a N-heterocyclic carbene metallacycle complex. Such materials and methods may be useful in the production of fine chemicals, advanced materials and specialty polymers.

19 Claims, 20 Drawing Sheets

OTHER PUBLICATIONS

César et al., Chiral N-Heterocyclic Carbenes as Stereodirecting Ligands in Asymmetric catalysis, Chem. Soc. Rev. 2004, 33, 619-636.

Cheng et al., Synthesis of N-Heteroary1-7-azabicyclo[2.2.1]heptane Derivatives via Palladium—Bisimidazol-2-ylidene Complex Catalyzed Amination Reactions, Org. Lett. 2001, 3(9), 1371-1374.

Chianese et al., Rhodium and Iridium Complexes of N-Heterocyclic Carbenes via Transmetalation: Structure and Dynamics. Organometallics. 2003;22(8):1663-1667.

Dorta et al., Stable, Three-Coordinate Ni(CO)2(NHC) (NHC=N-Heterocyclic Carbene) Complexes Enabling the Determination of Ni—NHC Bond Energies, J. Am. Chem. Soc. 2003, 125(35), 10490-10491.

Dorta et al., Steric and Electronic Properties of N-Heterocyclic Carbenes (NHC): A Detailed Study on Their Interaction with Ni(CO)4, J. Am. Chem. Soc. 2005, 127(8), 2485-2495.

Frey et al., A straight forward in situ preparation of NHC-substituted phosphapalladacycles. J Organometallic Chem. 2006;691:2403-2408.

Frey et al., Synthesis and Characterization of N-Heterocyclic Carbene Phospha-Palladacycles and Their Properties in Heck Catalysis. Organometallics. 2005;24:4416-4426.

Frisch et al., Comparison of palladium carbene and palladium phosphine catalysts for catalytic coupling reactions of aryl halides. J Mol Catal. 2004;214:231-239.

Goekce et al., The synthesis and structural characterization of a N-heterocyclic carbene-substituted palladacycle. J Coordination Chem. 2007;60:805-13. Abstract Only.

Grasa et al., Palladium/Imidazolium Salt Catalyzed Coupling of Aryl Halides with Hypervalent Organostannates, Org. Lett. 2001, 3(1), 119-122.

Gstöttmayr et al., A Defined N-Heterocyclic Carbene Complex for the Palladium-Catalyzed Suzuki Cross-Coupling of Aryl Chlorides at Ambient Temperatures, Angew. Chem. Int. Ed. 2002, 41(8), 1363-1365.

Hadei et al., Electronic nature of N-heterocyclic carbene ligands: effect on the Suzuki reaction. Org Lett. May 12, 2005;7(10):1991-4.

Hadei et al., The first Negishi cross-coupling reaction of two alkyl centers utilizing a Pd-N-heterocyclic carbene (NHC) catalyst. Org Lett. Aug. 18, 2005;7(17):3805-7.

Hadei et al., The first Negishi cross-coupling reaction of two alkyl centers utilizing a Pd-N-heterocyclic carbene (NHC) catalyst. Org Lett. Aug. 18, 2005;7(17):3805-7. Supporting Information.

Hahn, Heterocyclic Carbenes, Angew. Chem. Int. Ed. 2006, 45(9), 1348-1352.

Herrmann et al., N-Heterocyclic Carbenes, Angew. Chem. Int. Ed. 1997, 36, 2162-2187.

Herrmann, N-Heterocyclic carbenes: a new concept in organometallic catalysis, Angew. Chem. Int. Ed. 2002, 41, 1290-1309.

Hillier et al., A Combined Experimental and Theoretical Study Examining the Binding of N-Heterocyclic Carbenes (NHC) to the Cp*RuCl (Cp*=η5-C5Me5) Moiety: Insight into Stereoelectronic Differences between Unsaturated and Saturated NHC Ligands, . Organometallics 2003, 22(21), 4322-4326.

Hiraki et al., New Palladium(II) Carbene Complexes Containing a Cyclometallated Aryl Group. Bulletin Chem Society Japan. 1978;51:2548-50.

Huang et al., Efficient Cross-Coupling of Aryl Chlorides with Aryl Grignard Reagents (Kumada Reaction) Mediated by a Palladium/Imidazolium Chloride System, J. Am. Chem. Soc. 1999, 121(42), 9889-9890.

Huang et al., General and Efficient Catalytic Amination of Aryl Chlorides Using a Palladium/Bulky Nucleophilic Carbene System, Org. Lett. 1999, 1(8), 1307-1309.

Iyer et al., Mizoroki-Heck reaction, catalysis by nitrogen ligand Pd complexes and activation of aryl bromides. Synlett. 2004;60:2163-72.

Iyer et al., Saturated N-Heterocyclic Carbene Oxime and Amine Palladacyle Catalysis of the Mizoroki-Heck and the Suzuki Reactions. Synlett. 2003;8:1125-28.

Kantchev et al., Palladium complexes of N-heterocyclic carbenes as catalysts for cross-coupling reactions—a synthetic chemist's perspective. Angew Chem Int Ed Engl. 2007;46(16):2768-813.

Kantchev et al., Pd-N-Heterocyclic Carbene (NHC) Catalysts for Cross-Coupling Reactions. Aldrichimica Acta. 2006;39(4):97-111.

Kantchev et al., Practical Heck-Mizoroki coupling protocol for challenging substrates mediated by an N-heterocyclic carbene-ligated palladacycle. Org Lett. Sep. 18, 2008;10(18):3949-52. Epub Aug. 19, 2008.

Kantchev et al., Practical One-Pot, Three-Component Synthesis of N-Heterocyclic Carbene (NHC) Ligated Palladacycles Derived from N,N-Dimethylbenzylamine. Organometallics. 2009;28(1):289-299.

Lebel et al., Structure and Reactivity of "Unusual" N-Heterocyclic Carbene (NHC) Palladium Complexes Synthesized from Imidazolium Salts, J. Am. Chem. Soc. 2004, 126(16), 5046-5047.

Lee et al., Efficient Cross-Coupling Reactions of Aryl Chlorides and Bromides with Phenyl- or Vinyltrimethoxysilane Mediated by a Palladium/Imidazolium Chloride System, Org. Lett. 2000, 2(14), 2053-2055.

Marion et al., Modified (NHC)Pd(allyl)Cl (NHC=N-Heterocyclic Carbene) Complexes for Room-Temperature Suzuki-Miyaura and Buchwald-Hartwig Reactions, J. Am. Chem. Soc. 2006, 128(12), 4101-4111.

Milne et al., An Extremely Active Catalyst for the Negishi Cross-Coupling Reaction, J. Am. Chem. Soc. 2004, 126(4), 13028-13032.

Nair et al., N-Heterocyclic Carbenes: Reagents, Not Just Ligands!, Angew. Chem. Int. Ed. 2004, 43(39), 5130-5135.

Navarro et al.,Suzuki-Miyaura, alpha-ketone arylation and dehalogenation reactions catalyzed by a versatile N-heterocyclic carbene-palladacycle complex. J Org Chem. Jan. 20, 2006;71(2):685-92.

Navarro et al., Synthesis of novel (NHC)Pd(acac)C1 complexes (acac=acetylacetonate) and their activity in cross-coupling reactions. Tetrahedron. 2005;61:9716-9722.

O'Brien et al., "Easily Prepared Air- and Moisture-Stable Pd-NHC (NHC=N-Heterocyclic Carbene) Complexes: A Reliable, User-Friendly, Highly Active Palladium Precatalyst for the Suzuki-Miyaura Reaction," Chem. Eur. J. 2006, 12, 4743-4748.

O'Brien et al., Towards the rational design of palladium-N-heterocyclic carbene catalysts by a combined experimental and computational approach. Tetrahedron. 2005;61(41):9723-35.

Organ et al., Pd-PEPPSI-IPent: an active, sterically demanding cross-coupling catalyst and its application in the synthesis of tetra-ortho-substituted biaryls. Angew Chem Int Ed Engl. 2009;48(13):2383-7.

Organ et al., A User-Friendly, All-Purpose Pd-NHC (NHC=N-Heterocyclic Carbene) Precatalyst for the Negishi Reaction: A Step Towards a Universal Cross-Coupling Catalyst. Chem Eur. 2006;12:4749-4755.

Peh et al., Rational exploration of N-heterocyclic carbene (NHC) palladacycle diversity: a highly active and versatile precatalyst for Suzuki-Miyaura coupling reactions of deactivated aryl and alkyl substrates. Chemistry. Apr. 6, 2010;16(13):4010-7.

Perry et al., Chiral N-Heterocyclic Carbene Complexes in Asymmetric Catalysis, Tetrahedron: Asymmetry 2003, 14, 951-961.

Seayad et al., Organocatalytic synthesis of N-Phenylisoxazolidin-5-ones and a one-pot synthesis of beta-amino acid esters. Org Lett. Mar. 6, 2008;10(5):953-6. Epub Feb. 5, 2008.

Shauffer et al., High turnover number and rapid, room-temperature amination of chloroarenes using saturated carbene ligands. Org Lett. May 18, 2000;2(10):1423-6.

Singh et al., Simple (Imidazol-2-ylidene)-Pd-Acetate Complexes as Effective Precatalysts for Sterically Hindered Suzuki-Miyaura Couplings, Org. Lett. 2005, 7(9), 1829-1832.

Viciu et al., Synthetic and Structural Studies of (NHC)Pd(allyl)Cl Complexes (NHC=N-heterocyclic carbene), Organometallics 2004, 23(7), 1629-1635.

Viciu et al., Synthesis, Characterization, and Catalytic Activity of N-Heterocyclic Carbene (NHC) Palladacycle Complexes. Org Lett. 2003;5(9):1479-1482.

Voutchkova et al., Disubstituted Imidazolium-2-Carboxylates as Efficient Precursors to N-Heterocyclic Carbene Complexes of Rh, Ru, Ir, and Pd, J. Am. Chem. Soc. 2005, 127(50), 17624-17625.

Walker et al., A Rationally Designed Universal Catalyst for Suzuki-Miyaura Coupling Processes, Angew. Chem. Int. Ed. 2004, 43(14), 1871-1876.

Wong et al., N-heterocyclic carbene (NHC)-catalyzed direct amidation of aldehydes with nitroso compounds. Org Lett. Jun. 19, 2008;10(12):2333-6. Epub May 14, 2008.

Yin et al., A Highly Active Suzuki Catalyst for the Synthesis of Sterically Hindered Biaryls: Novel Ligand Coordination, J. Am. Chem. Soc. 2002, 124(7), 1162-1163.

Zapf et al., Practical synthesis of new and highly efficient ligands for the Suzuki reaction of aryl, Chem. Commun. 2004, 38-39.

Zapf et al., The Development of Efficient Catalysts for Palladium-catalyzed Coupling Reactions of Aryl Halides, Chem. Commun. 2005, 431-440.

Zhang et al., The first N-heterocyclic carbene-based nickel catalyst for C-S coupling. Org Lett. Aug. 30, 2007;9(18):3495-8. Epub Aug. 4, 2007.

Bedford et al., N-Heterocyclic carbene adducts of orthopalladated triarylphosphite complexes, Dalton Trans. 2005,2774-2779. First published as Advance Article on the Web Jul. 15, 2005.

Brenstrum et al., Phosphaadamantanes as Ligands for Palladium Catalyzed Cross-Coupling Chemistry: Library Synthesis, Characterization, and Screening in the Suzuki Coupling of Alkyl Halides and Tosylates Containing β-Hydrogens with Boronic Acids and Alkylboranes. J Org. Chem. 2004, 69(22), 7635-7639. Epub Sep. 30, 2004.

Chasse et al., Towards a computed structure database: Modular and systematic approach to develop effective Pd-N-heterocyclic carbene catalysts for cross-coupling reactions. Abstracts of Papers of the American Chemical Society. Aug. 2005;230:U3238.

Dowlut et al., An efficient low-temperature Stille-Migita cross-coupling reaction for heteroaromatic compounds by Pd-PEPPSI-IPent. Chemistry. Apr. 12, 2010;16(14):4279-83.

Dupont et al., The Potential of Palladacycles: More Than Just Precatalysts, J. Chem. Rev. 2005, 105(6), 2527-2571. Epub May 20, 2005.

Furstner et al., General and User-friendly Method for Suzuki Reactions with Aryl Chlorides. Synlett. 2001;2:290-292.

Grasa et al., Amination Reactions of Aryl Halides with Nitrogen-Containing Reagents Mediated by Palladium/Imidazolium Salt Systems. J Org Chem 2001;66:7729-7737. Epub Oct. 25, 2001.

Hadei et al., Room-temperature Negishi cross-coupling of unactivated alkyl bromides with alkyl organozinc reagents utilizing a Pd/N-heterocyclic carbene catalyst. J. Org. Chem. 2005, 70(21), 8503-8507. Epub Sep. 9, 2005.

Harkal et al., Dialkylphosphinoimidazoles as New Ligands for Palladium-Catalyzed Coupling Reactions of Aryl Chlorides. Adv Synth Catal. 2004;346:1742-1748.

Kantchev et al., Electronic and steric tuning of N-heterocyclic carbene ligands: Effect on palladium-catalyzed cross-coupling reactions. Abstracts of Papers of the American Chemical Society. Aug. 2005;230:U3240.

Lee et al., Improved Catalysts for the Palladium-Catalyzed Synthesis of Oxindoles by Amide α-Arylation. Rate Acceleration, Use of Aryl Chloride Substrates, and a New Carbene Ligand for Asymmetric Transformations, J. Org. Chem. 2001, 66, 3402-3415. Epub Apr. 21, 2001.

Malatesta et al., Palladium(0) compounds. Part II. Compounds with triarylphosphines, triaryl phosphites, and triarylarsines, J. Chem. Soc. 1957, 1186-1188.

Marion et al., (IPr)Pd(acac)Cl: An Easily Synthesized, Efficient, and Versatile Precatalyst for C—N and C—C Bond Formation, J. Org. Chem. 2006, 71(10), 3816-3821. Epub Apr. 11, 2006.

O'Brien et al., User-friendly palladium-N-heterocyclic carbene (NHC) complexes for coupling reactions: Employing a throw away ligand approach. Abstracts of Papers of the American Chemical Society. Aug. 2005;230:U3238-39.

Organ et al., Pd-catalyzed aryl amination mediated by well defined, N-heterocyclic carbene (NHC)-Pd precatalysts, PEPPSI. Chemistry. 2008;14(8):2443-52. Epub Jan. 25, 2008.

Rataboul et al., New Ligands for a General Palladium-Catalyzed Amination of Aryl and Heteroaryl Chlorides. Chem. Eur. J. 2004, 10(12), 2983-2990. Epub Apr. 28, 2004.

Yang et al., A Highly Efficient Palladium/Imidazolium Salt System for Catalytic Heck Reactions. Synlett. 2001;10:1539-1542.

* cited by examiner

N-HETEROCYCLIC CARBENE METALLACYCLE CATALYSTS AND METHODS

RELATED APPLICATION

This application is a national stage filing under 35 U.S.C. § 371 of International Patent Application No. PCT/US2007/014393, filed Jun. 20, 2007, the contents of which are incorporated herein by reference in its entirety for all purposes.

FIELD OF THE INVENTION

The present invention relates to N-heterocyclic carbene-ligated metallacycle catalysts and precatalysts, and related methods.

BACKGROUND OF THE INVENTION

Transition metal-catalyzed cross-coupling reactions are useful in a wide range of chemical transformations that have application in pharmaceuticals and materials chemistry. The transition metal catalyst plays a key role in the catalytic cycle. For example, transition metals such as Pd may be ligated with suitable spectator ligands that stabilize the metal center and impart the reactivity patterns required for catalytic performance. Tertiary phosphines are among the most widely used precatalyst ligands for cross-coupling reactions. One of the most widely-used Pd-phosphine catalyst systems today is based on triphenylphosphine ($PPh_3$). However, such catalyst systems often display moderate reactivity and substrate scope. In some cases, the catalyst or precatalyst system, such as $[Pd(PPh_3)_4]$, exhibits a short shelf life and readily decomposes upon storage. Other phosphine ligands have been developed, but many require multi-step syntheses and, thus, are often high in cost. Moreover, a number of phosphines are toxic, air-sensitive and even pyrophoric.

As an alternative to phosphine ligands, N-heterocyclic carbenes (NHCs) have been shown to impart greater stability and increased catalytic activity in transition metal-mediated homogeneous catalysis, relative to phosphines. NHCs have stronger sigma-donating properties relative to phosphine ligands, resulting in stronger bonds formed with the transition metal center. NHC ligands based on 1,3-diarylimidazol-2-ylidenes and their 4,5-dihydro analogs are often used with a Pd metal center. NHCs are typically highly air-sensitive and moisture-sensitive, and metal complexes comprising NHCs are often prepared in situ by deprotonation of the corresponding (4,5-dihyrdo)imidazolium salts. For example, some catalytic systems may involve the separate addition of various components of the catalytically active species (e.g., metal source, salts of carbene ligands, etc.) for the in situ formation of the catalytically active species. However, while such catalyst systems have been shown to be useful, in many cases it may be difficult to control the amount and/or chemical composition of the catalytically active species formed.

Accordingly, improved methods are needed.

SUMMARY OF THE INVENTION

The present invention provides methods for synthesizing a transition metal-containing precatalyst comprising reacting at least three components all contained together in a single reaction chamber to form a transition metal-containing precatalyst having one of the following structures,

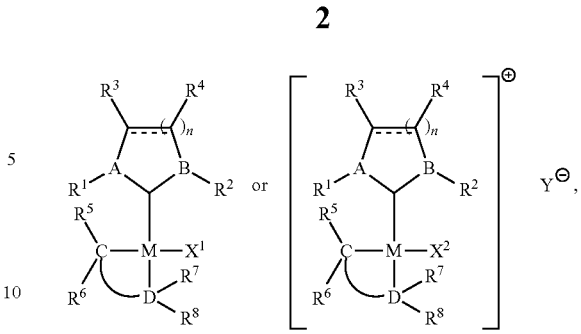

wherein M is Pd, Pt, or Ru; each $R^{1-8}$ is independently absent, hydrogen, alkyl, cycloalkyl, heteroalkyl, cycloheteroalkyl, aryl, heteroaryl, or a substituted derivative thereof, or wherein any two of $R^{1-8}$ are joined to form a cycloalkyl, cycloheteroalkyl, aryl, heteroaryl, or substituted derivative thereof; A is carbon or a heteroatom; B is a heteroatom; C is alkyl or aryl; D is a heteroatom; $X^1$ is halide, sulfonate, or carboxylate; $X^2$ is a neutral ligand; Y is a counterion; ⌒ is alkyl, heteroalkyl, aryl, heteroaryl, or a substituted derivative thereof; ----- is a single bond or double bond; and n is an integer between 1 and 3.

The present invention also relates to compositions of matter comprising a compound having one of the following structures,

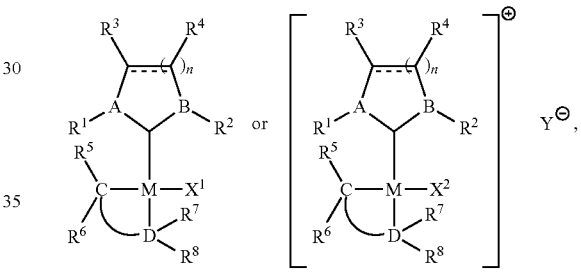

wherein M is Pd, Pt, or Ru; each $R^{1-8}$ is independently absent, hydrogen, alkyl, cycloalkyl, heteroalkyl, cycloheteroalkyl, aryl, heteroaryl, or a substituted derivative thereof, or wherein any two of $R^{1-8}$ are joined to form a cycloalkyl, cycloheteroalkyl, aryl, heteroaryl, or substituted derivative thereof; A is carbon or a heteroatom; B is a heteroatom; C is alkyl or aryl; D is a heteroatom; $X^1$ is halide, sulfonate, or carboxylate; $X^2$ is a neutral ligand; Y is a counterion; ⌒ is alkyl, heteroalkyl, aryl, heteroaryl, or a substituted derivative thereof; ----- is a single bond or double bond; and n is an integer between 1 and 3; wherein the compound does not have the following structure,

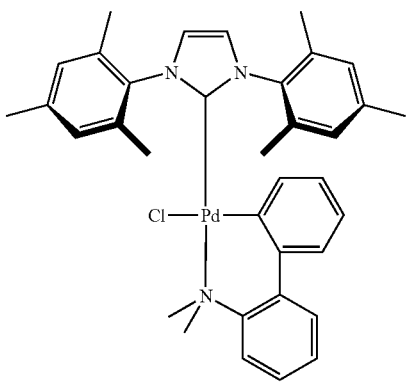

-continued
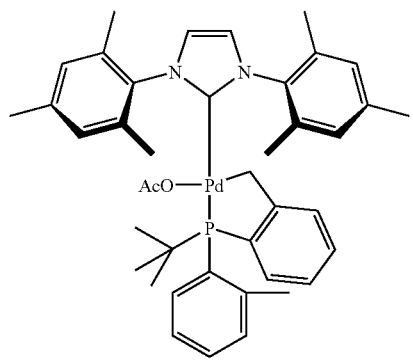
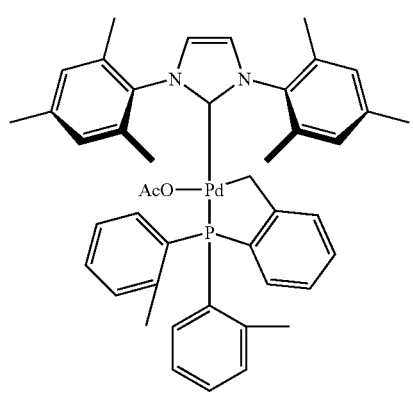
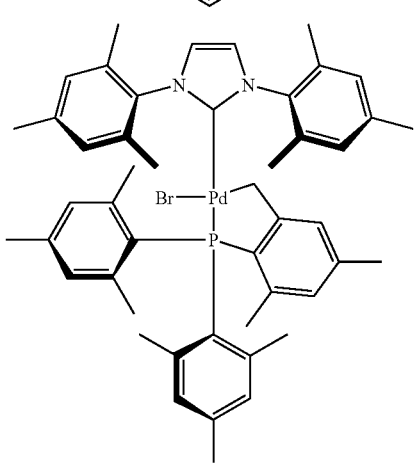
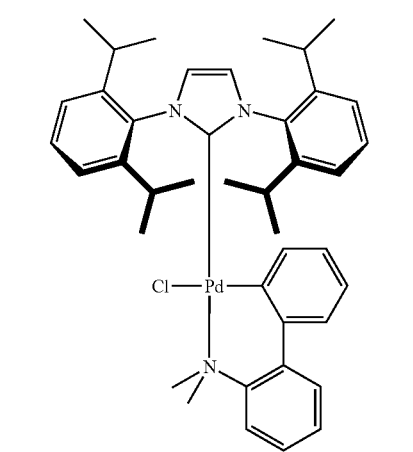
-continued
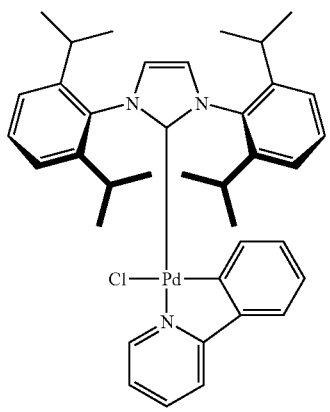
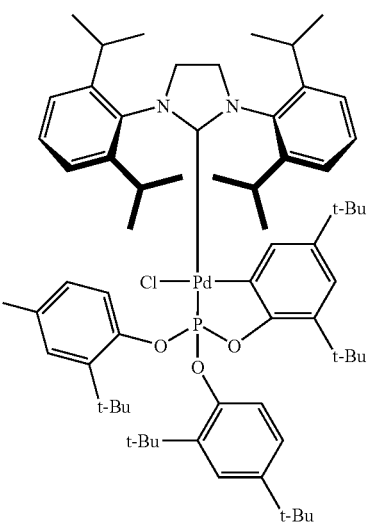
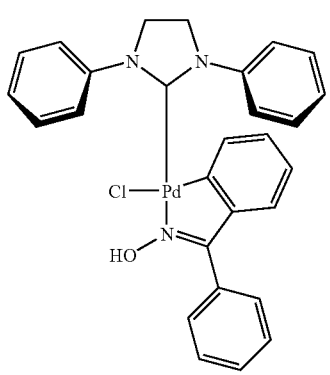
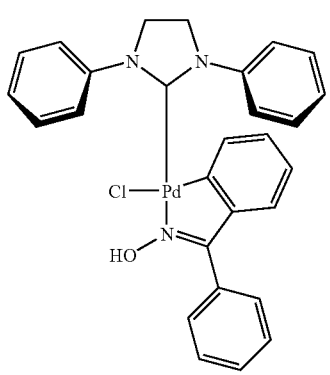

5
-continued
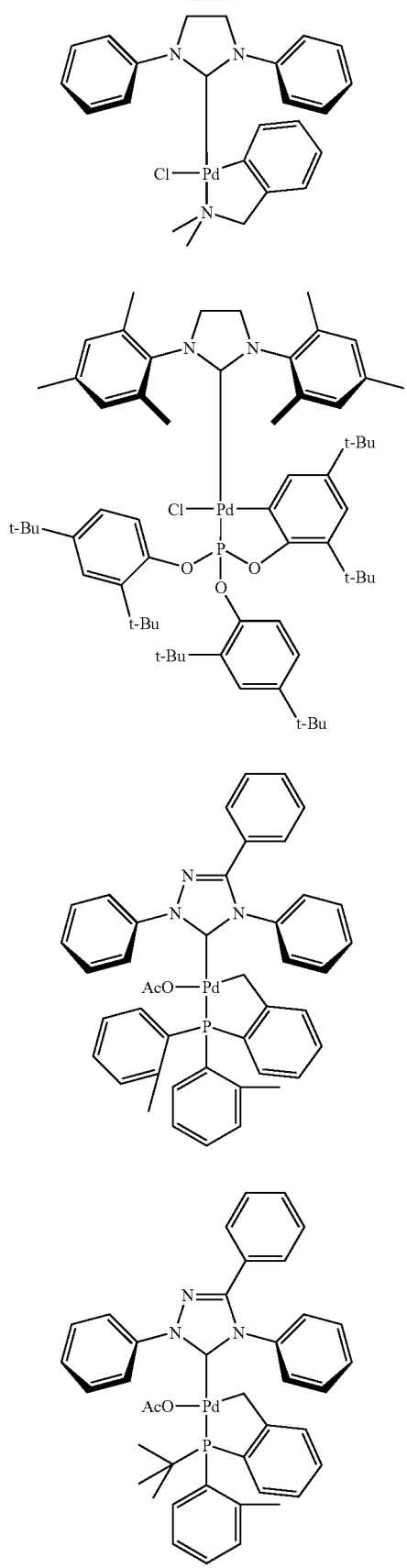
6
-continued
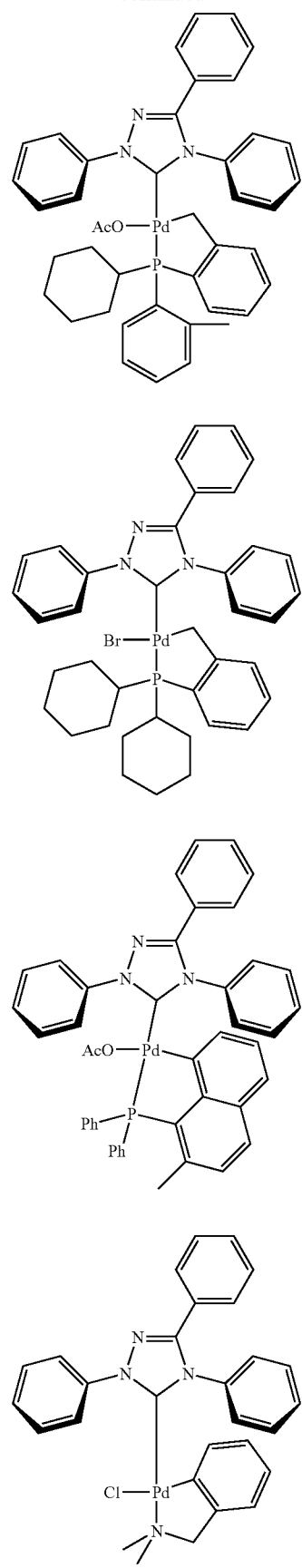

-continued
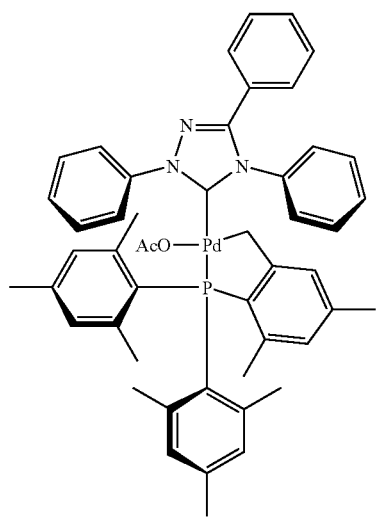
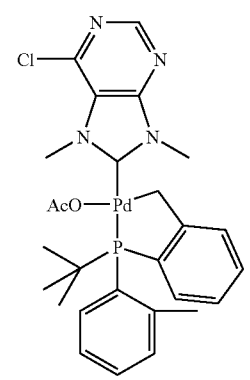
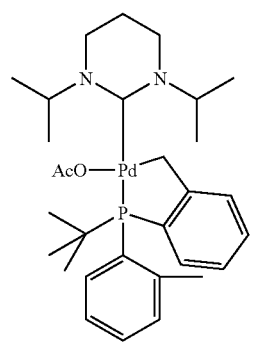
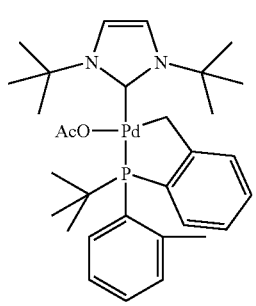
-continued
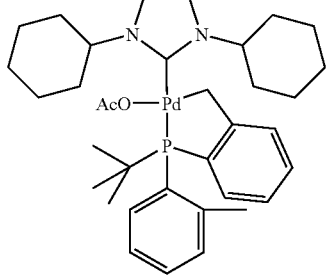
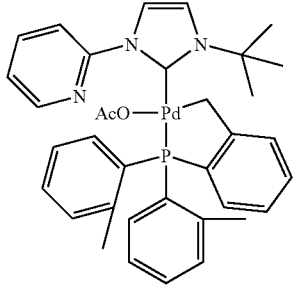
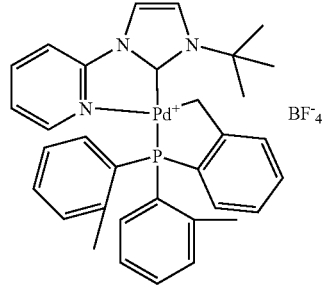
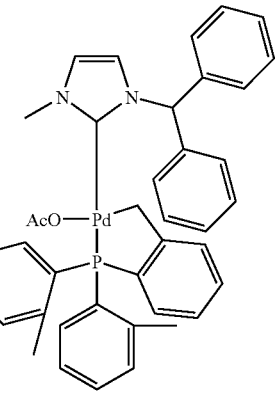
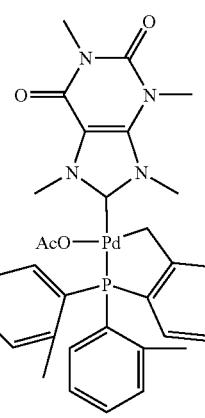

-continued

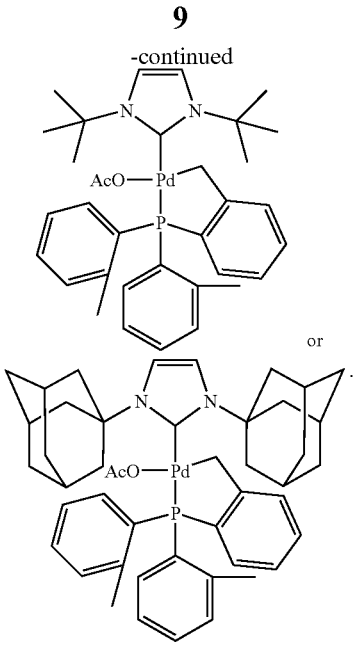

The present invention also relates to compositions of matter comprising a compound having the following structure,

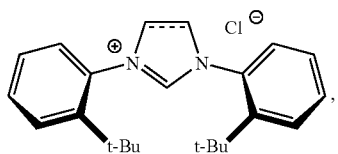

wherein ----- is a single bond or double bond.

The present invention also relates to compositions of matter comprising a compound having the following structure,

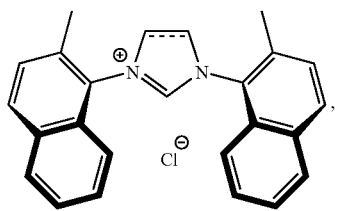

wherein ----- is a single bond or double bond.

DETAILED DESCRIPTION

The present invention generally relates to materials and methods for catalytic reactions, including transition metal-catalyzed cross-coupling reactions.

Materials and methods of the present invention may be useful in various metal-catalyzed processes, such as cross-coupling of compounds to form carbon-carbon bonds and/or carbon-heteroatom bonds. In some cases, materials of the invention advantageously may be synthesized in one synthetic step without the need for isolation of intermediate compounds. The materials may be stable metal complexes that do not require special handling or processing conditions, such as the exclusion of air, water, and the like. Also, materials of the invention may be synthesized from inexpensive and readily available starting materials, under relatively mild reaction conditions and in high yield. Such materials and methods may be useful in the production of fine chemicals, advanced materials, and specialty polymers.

In some embodiments, the present invention provides stable (e.g., isolable) metal complexes comprising a carbene ligand, such as an N-heterocyclic carbene ligand. The metal complex may further comprise additional ligands, including neutral ligands and charged ligands, which may enhance performance of the catalyst. In some cases, the metal complexes may act as catalysts (e.g., in cross-coupling reactions) or may be precatalysts that are readily activated to catalyze cross-coupling reactions. As used herein, a "precatalyst" may refer to a chemical species which, upon activation, may produce an active catalyst species in a reaction. For example, a metal complex may comprise a ligand which, upon activation, dissociates from the metal complex to generate the catalytically active species. In some cases, the precatalyst may be isolated as a stable compound. As used herein, the term "catalyst" includes active forms of the catalyst participating in the reaction as well as catalyst precursors (e.g., precatalysts) that may be converted in situ into the active form of the catalyst. In some embodiments, catalysts of the invention may be advantageous in that the chemical composition, amount, and/or release of the catalytically active species may be controlled.

Figure 2:
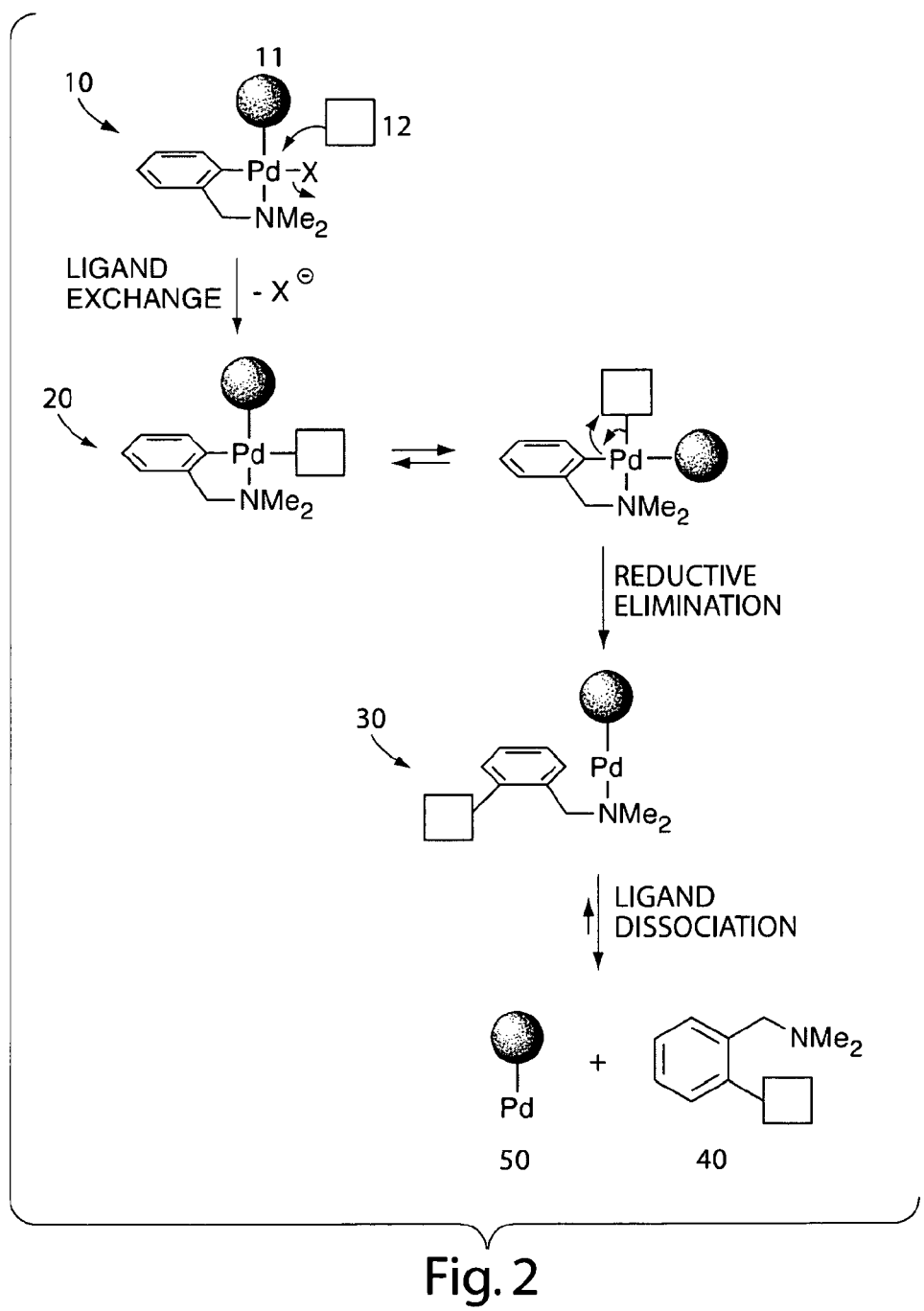
FIG. 2 shows a proposed mechanism for activation of a precatalyst of the present invention to form a catalytically active species, according to one embodiment of the invention.

In some embodiments, a metal complex of the invention may comprise an N-heterocyclic carbene ligand coordinated to a catalytic metal center and a bidentate ligand that, when bound to the metal center, forms a metallacycle that may aid in stabilizing the metal complex. Upon exposure of the metal complex to an activating agent, the bidentate ligand may be converted to a species which may dissociate from the metal center, generating the catalytically active metal species. As shown in the illustrative embodiment shown in FIG. 2, compound 10 comprising an N-heterocyclic carbene ligand (11) and a bidentate ligand may undergo ligand exchange with activating agent (12) to produce compound 20. A bond between activating agent 12 and the bidentate ligand may be formed via reductive elimination to produce compound 30, which may then undergo ligand disassociation to afford product 40 and the active catalyst 50. In some embodiments, the activating agent may be a nucleophile. In an illustrative embodiment, the activating agent maybe a hydride generated in situ from a component of the reaction mixture capable of hydride transfer to the metal center (e.g., Pd). The activating agent can be introduced into the mixture either separately or in combination with (e.g., premixed with) the precatalyst. Such activating agents may include, but are not limited to, formate salts, organometallic derivatives, $NaBH_4$ or $iBu_2AlH$ or $LiAlH_4$ and compounds derived thereof.

Catalysts of the invention may be useful in transition metal-catalyzed cross-coupling methodologies, including the Suzuki-Miyaura, Heck-Mizoroki, Negishi, Stille, Kumada-Tamao-Corriu, and Sonogashira cross-coupling reactions, and the like. The catalysts may comprise a transition metal center, such as palladium, platinum, or ruthenium, and an N-heterocyclic carbene ligand, which may serve to modulate catalyst performance, as known to those of ordinary skill in the art.

Figure 9:
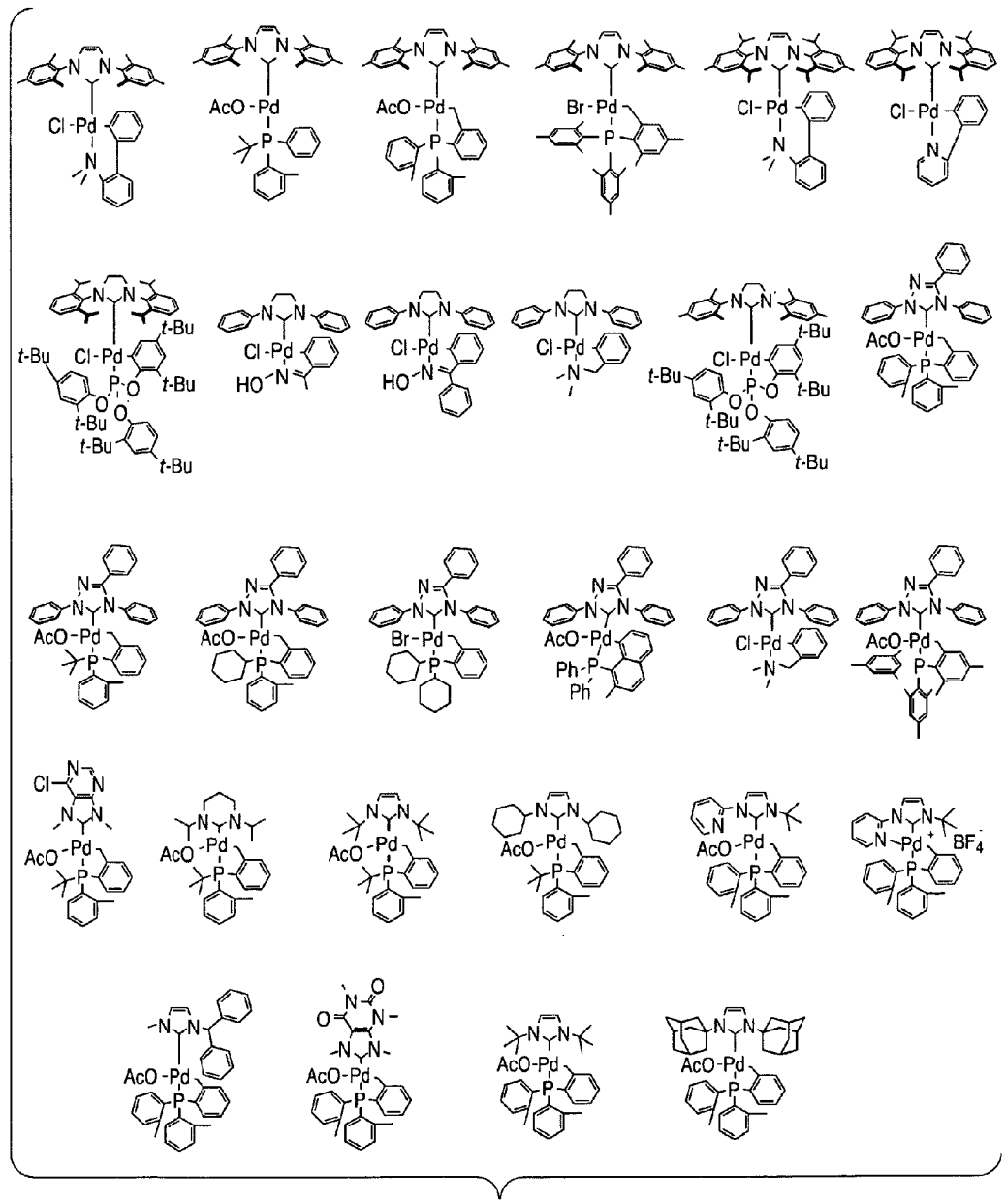
FIG. 9 shows examples of known NHC-ligated palladacycles.

In some embodiments, the present invention provides transition metal complexes suitable for use in such cross-coupling reactions. The present invention provides compositions of matter comprising compounds having one of the following structures,

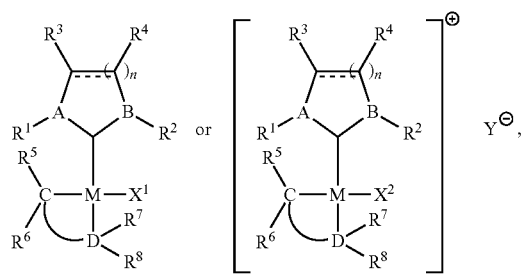

wherein M is Pd, Pt, or Ru; each $R^{1-8}$ is independently absent, hydrogen, alkyl, cycloalkyl, heteroalkyl, cycloheteroalkyl, aryl, heteroaryl, or a substituted derivative thereof, or wherein any two of $R^{1-8}$ are joined to form a cycloalkyl, cycloheteroalkyl, aryl, heteroaryl, or substituted derivative thereof; A is carbon or a heteroatom; B is a heteroatom; C is alkyl or aryl; D is a heteroatom; $X^1$ is a halide, sulfonate, or carboxylate; $X^2$ is a neutral ligand; Y is a counterion; ⌞ an is alkyl, heteroalkyl, aryl, heteroaryl, or a substituted derivative thereof; ----- is a single bond or double bond; and n is an integer between 1 and 3; wherein the compound does not have any of the structures shown in FIG. 9. In some cases, Y is a non-coordinating counterion, such as tetrafluoroborate, hexafluorophosphate or tetraarylborate).

In some cases, each $R^{1-8}$ is independently hydrogen, alkyl, cycloalkyl, alkoxy, amino, aryl, heteroaryl, or substituted derivatives thereof; A is carbon, nitrogen, phosphorus, oxygen, or sulfur; B is nitrogen, phosphorus, oxygen, or sulfur; D is nitrogen, phosphorus, arsenic, antimony, oxygen, sulfur, selenium, or tellurium; and n is an integer between 1 and 3.

For example, in some embodiments, A and B are nitrogen; D is nitrogen, phosphorus, or sulfur; $R^1$ and $R^2$ are aromatic rings optionally substituted with methyl, ethyl, isopropyl, t-butyl, methoxy, isopropoxy, trifluoromethyl, or phenyl; $R^3$ and $R^4$ are phenyl, t-butyl, or are joined together to form a six-membered ring; $R^5$ and $R^6$ are hydrogen, t-butyl, methoxy, trifluoromethyl, or are joined together to form an aryl ring; $R^7$ and $R^8$ are methyl, isopropyl, t-butyl, phenyl, phenoxy, hydroxyl, $R^7$ and $R^8$ are joined together to form a ring; or at least one of $R^7$ and $R^8$ is joined to a portion of ⌞ to form a ring.

In one set of embodiments, M is Pd, $R^1$ and $R^2$ are aromatic rings substituted with ethyl, methyl, isopropyl, tertiary butyl, or combinations thereof, A and B are nitrogen, and D is nitrogen or phosphorus. In some cases, $R^1$ and $R^2$ are aromatic rings substituted at the ortho positions relative to A and/or B.

In one set of embodiments, the compound is a salt comprising the metal complex and a counterion (e.g., "Y"). The counterion Y may be a weak or non-nucleophilic stabilizing ion, such that activation of a precatalyst may be enhanced and/or undesired side reactions may be reduced. In some cases, the counterion is a non-coordinating ion, wherein substitution of the counterion with a different group may occur rapidly and/or with ease, to generate a catalytically active species. For example, the counterion may be $BF_4$, $PF_6$, or $Ar_4B$, wherein Ar is aryl. When the compound is a salt, the metal complex may further comprise a neutral ligand to occupy a vacant coordination site. For example, the neutral ligand may be a nitrite (e.g., acetonitrile), ether (e.g., tetrahydrofuran), or alcohol (e.g., methanol). The catalyst complex may include additional ligands, such as halides, carboxylates, and the like, as required to obtain a stable complex.

In one embodiment, the compound has the following structure,

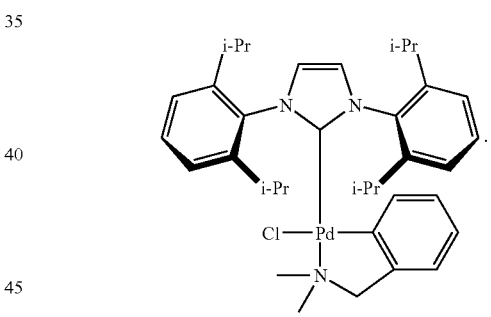

In one embodiment, the compound has the following structure,

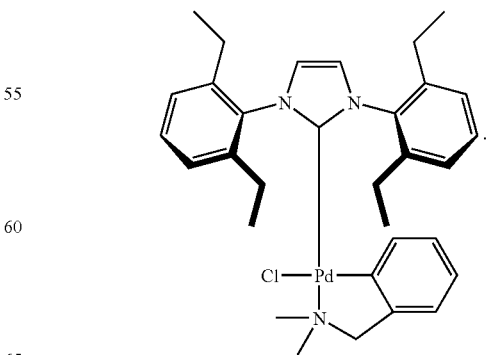

In one embodiment, the compound has the following structure,

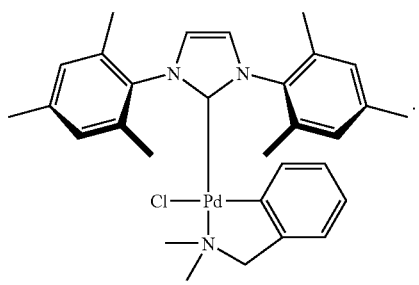

In one embodiment, the compound has the following structure,

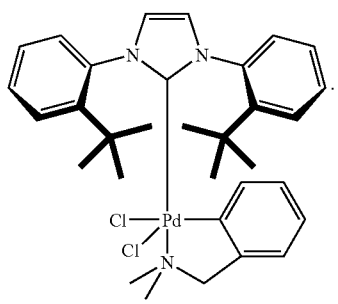

In one embodiment, the compound has the following structure,

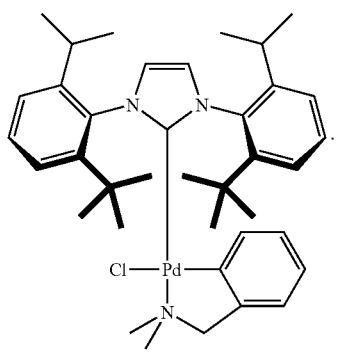

In one embodiment, the compound has the following structure,

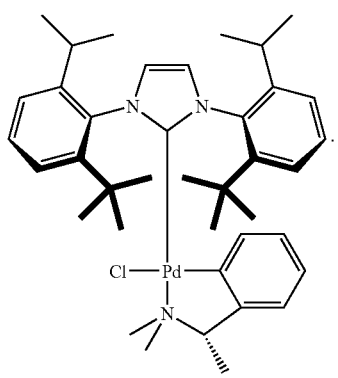

In one embodiment, the compound has the following structure,

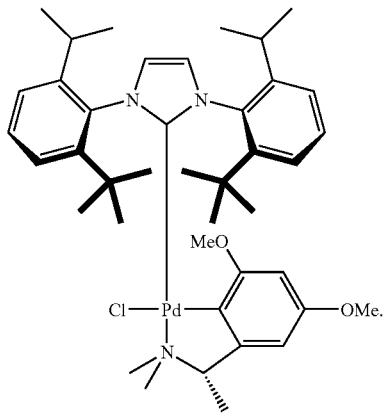

In one embodiment, the compound has the following structure,

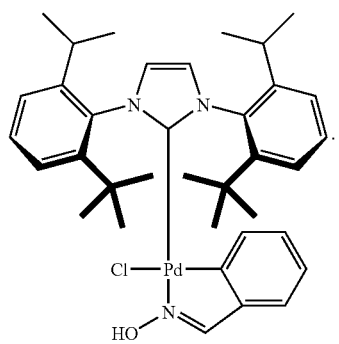

In one embodiment, the compound has the following structure,

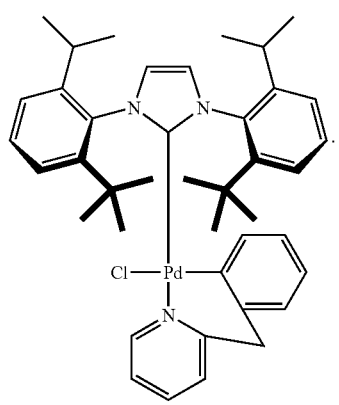

In one embodiment, the compound has the following structure,

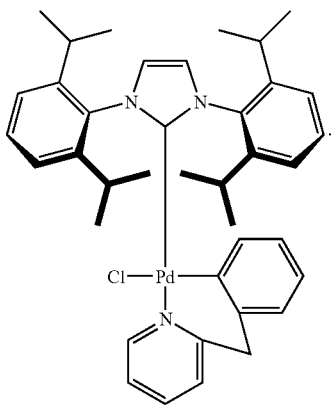

In some embodiments, the transition metal-containing precatalyst is stable in the presence of oxygen. In some embodiments, the transition metal-containing precatalyst is stable in the presence of water.

The present invention also provides methods for synthesizing transition metal-containing catalysts and/or precatalysts as described herein. In some embodiments, the method comprises reacting at least three components all contained together in a single reaction chamber to form a transition metal-containing precatalyst having one of the following structures,

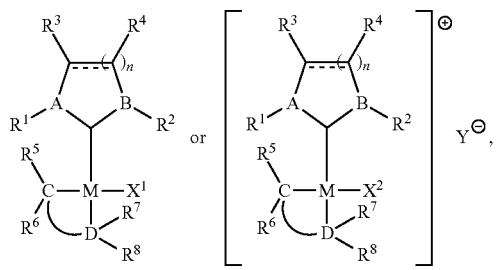

wherein M is Pd, Pt, or Ru; each $R^{1-8}$ is independently absent, hydrogen, alkyl, cycloalkyl, heteroalkyl, cycloheteroalkyl, aryl, heteroaryl, or a substituted derivative thereof, or wherein any two of $R^{1-8}$ are joined to form a cycloalkyl, cycloheteroalkyl, aryl, heteroaryl, or substituted derivative thereof; A is carbon or a heteroatom; B is a heteroatom; C is alkyl or aryl; D is a heteroatom; $X^1$ is halide or carboxylate; $X^2$ is a neutral ligand; Y is a counterion; ⌒ is alkyl, heteroalkyl, aryl, heteroaryl, or a substituted derivative thereof; ----- is a single bond or double bond; and n is an integer between 1 and 3.

One component of the reaction may be a metal source comprising a metal atom that, upon reaction, may form the metal center of the catalyst. For example, the metal source may comprise salts or coordination compounds of palladium, platinum, or ruthenium. Another component of the reaction may be an N-heterocyclic carbene ligand precursor, such as an imidazolium salt, for example. As used herein, an "N-heterocyclic carbene ligand precursor" refers to a chemical moiety containing a species that may be reacted to form an N-heterocyclic carbene ligand that coordinates the metal center. Another component of the reaction may be a bidentate ligand, as described herein. The method may further comprise the addition of other reagents, such as a base, inorganic salt, neutral ligand, and/or solvent, to facilitate the reaction. In some cases, the reagent may form a bond with the metal complex. For example, a neutral ligand may be added to the reaction mixture, wherein the neutral ligand coordinates the metal center. In some cases, the reagent may not form a bond with the metal complex, but serves to otherwise promote the formation of the metal complex.

In one embodiment, at least one of the three components is a palladium-containing compound. The palladium-containing may be $PdCl_2$ or $(CH_3CN)_2PdCl_2$, for example.

In some embodiments, at least one of the three components is an N-heterocyclic carbene ligand precursor. The N-heterocyclic carbene ligand precursor may have the structure,

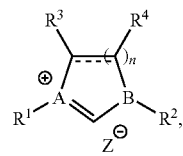

wherein each $R^{1-4}$ is independently absent, hydrogen, alkyl, cycloalkyl, heteroalkyl, cycloheteroalkyl, aryl, heteroaryl, or a substituted derivative thereof, or wherein any two of $R^{1-4}$ are joined to form a cycloalkyl, cycloheteroalkyl, aryl, heteroaryl, or substituted derivative thereof; A is carbon or a heteroatom; B is a heteroatom; ----- is a single bond or double bond; n is an integer between 1 and 3; and Z is halide, carboxylate, $BF_4$, $PF_6$, or $Ar_4B$, wherein Ar is aryl.

Figure 6A:
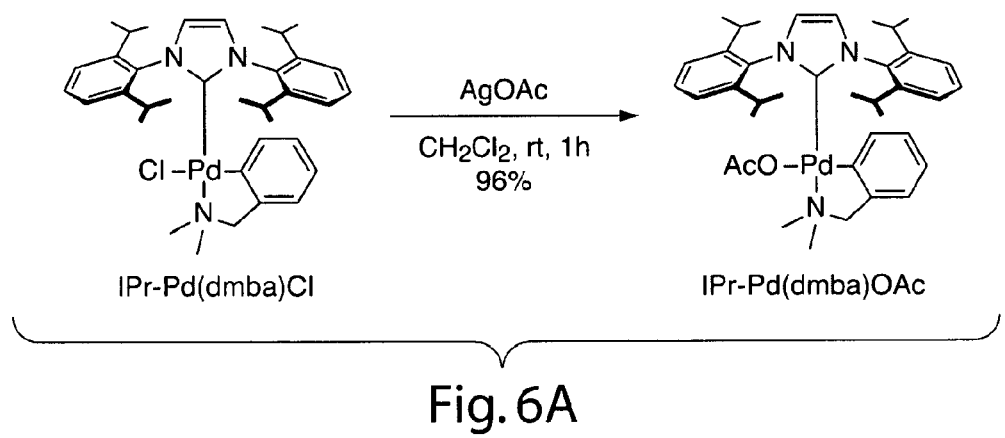
FIG. 6 shows a ligand exchange reaction to produce (a) IPr—Pd(dmba)OAc and (b) IPr—Pd(dmba)OCOCF$_3$.
Figure 6B:
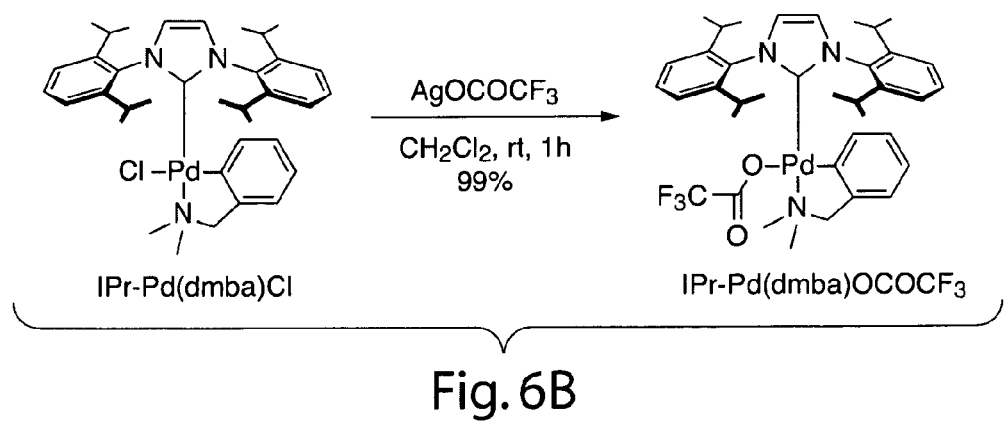

Precatalysts of the invention may be further reacted, for example, to replace the counterion (e.g., anion) with a different counterion. For example, a precatalyst of the invention may be reacted via an anion exchange reaction to involving exposure of the precatalyst to a metal salt or other species comprising a counterion. In some embodiments, a precatalyst comprising a halide (e.g., chloride) atom as the counterion may be treated with a metal salt, such as a silver salt comprising an anion, resulting in replacement of the halide on the precatalyst with the anion of the silver salt and formation of a silver halide. In some cases, the anion exchange may be performed in a solvent (e.g., $CH_2Cl_2$) selected such that the silver halide is substantially insoluble in the solvent, facilitating purification of the precatalyst. Examples of such anion exchange reactions are shown in FIGS. 6A-B. Those of ordinary skill in the art would be able to identify other methods for anion exchange reactions useful in the context of the invention.

Figure 3A:
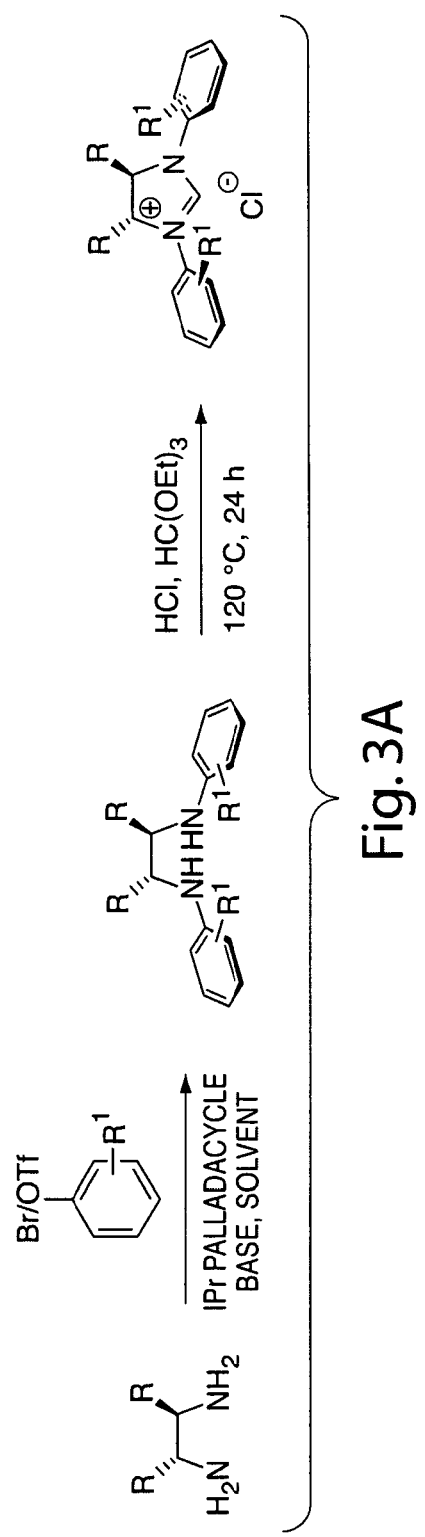
FIG. 3A shows a general synthesis of saturated N-heterocyclic carbene ligand precursors.

N-heterocyclic carbene ligand precursors may be synthesized according to methods known in the art. For example, in one embodiment, the N-heterocyclic carbene ligand precursor is an N-heterocyclic carbene salt, which may be synthesized by the cross-coupling of a substituted ethylene diamine derivative and an aryl halide or aryl triflate, followed by cyclization to form the N-heterocyclic carbene salt (FIG. 3A). In other embodiments, the N-heterocyclic carbene ligand precursor may be synthesized by condensation of amines with glyoxal, followed by cyclization to form the N-heterocyclic carbene salt, as shown in the illustrative embodiments in FIGS. 3B-C.

In one embodiment, the N-heterocyclic carbene ligand precursor has the structure,

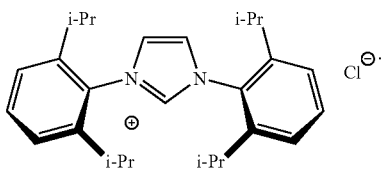

In one embodiment, the N-heterocyclic carbene ligand precursor has the structure,

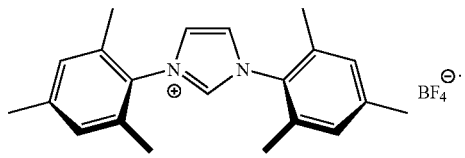

In one embodiment, the N-heterocyclic carbene ligand precursor has the structure,

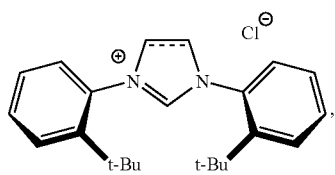

wherein ----- is a single bond or double bond. In some cases, ----- is a single bond. In some cases, ----- is a double bond.

In one embodiment, the N-heterocyclic carbene ligand precursor has the structure,

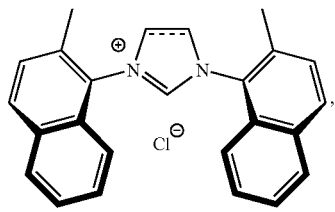

wherein ----- is a single bond or double bond. In some cases, ----- is a single bond. In some cases, ----- is a double bond.

In some embodiments, at least one of the three components is a compound having the structure,

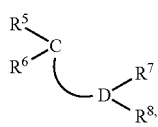

wherein each $R^{5-8}$ is independently absent, hydrogen, alkyl, cycloalkyl, heteroalkyl, cycloheteroalkyl, aryl, heteroaryl, or a substituted derivative thereof, or wherein any two of $R^{5-8}$ are joined to form a cycloalkyl, cycloheteroalkyl, aryl, heteroaryl, or substituted derivative thereof; C is alkyl or aryl; D is a heteroatom; X is halide or carboxylate; ⌒ is alkyl, heteroalkyl, aryl, heteroaryl, or a substituted derivative thereof.

In some embodiments, the palladium-containing compound, the N-heterocyclic carbene and the ligand are not joined by a bond prior to the reacting step.

In some embodiments, the method is represented by Scheme 1,

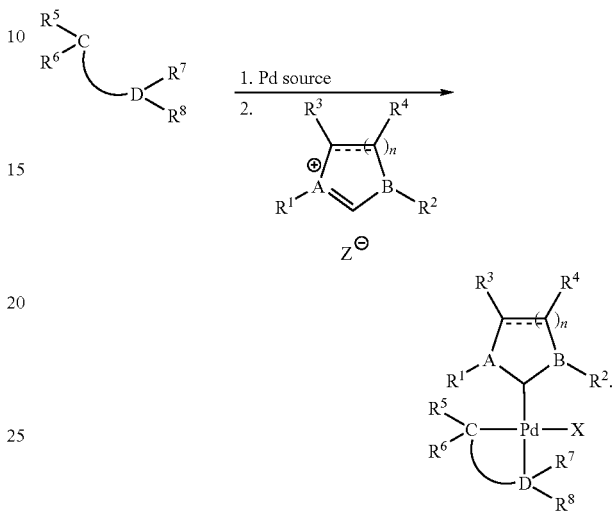

Figure 1:
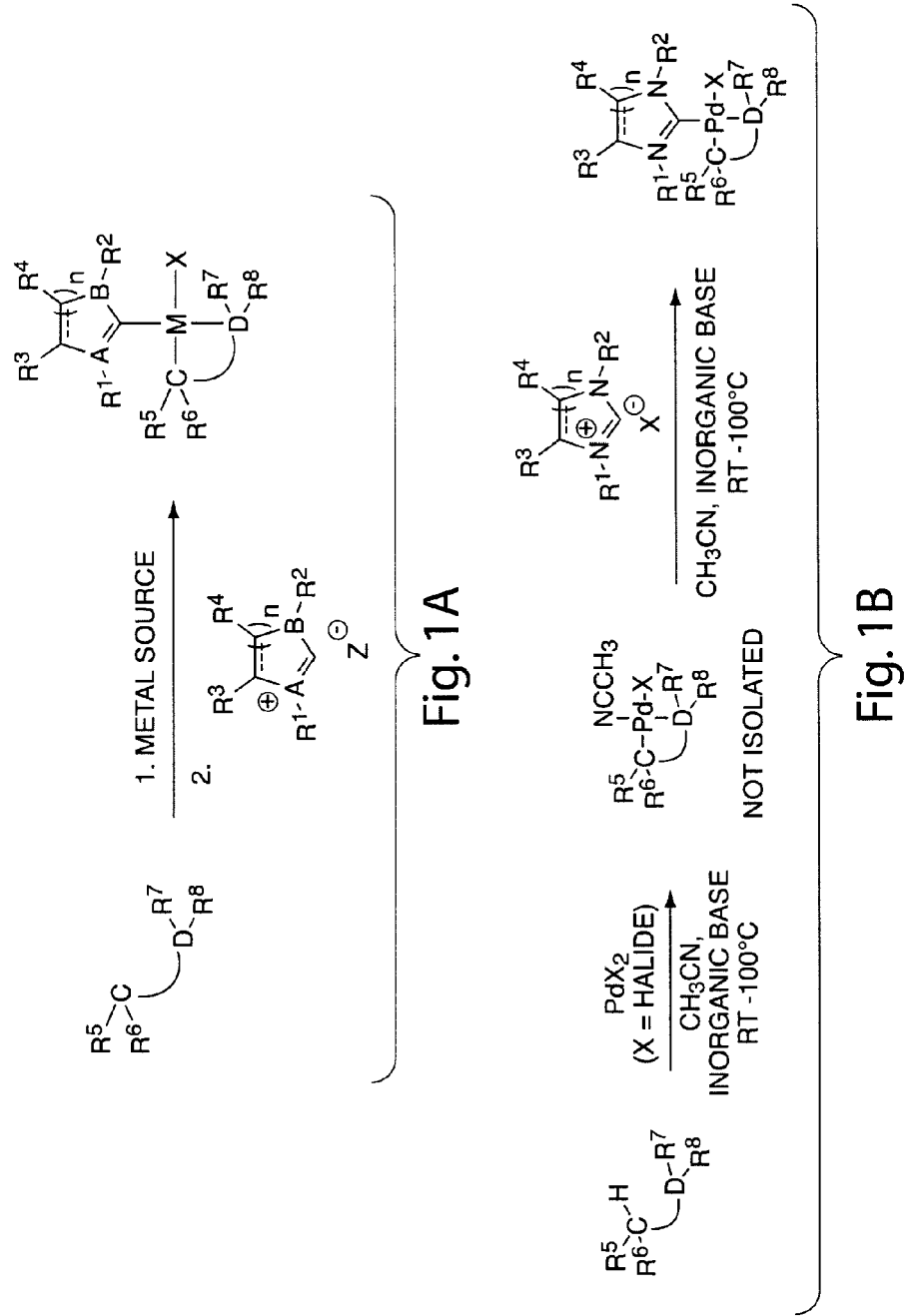
FIG. 1A shows the one-pot synthesis of precatalysts, according to one embodiment of the invention.
FIG. 1B shows the one-pot synthesis of a precatalyst comprising an imidazolium carbene ligand, using a Pd salt in acetonitrile, according to one embodiment of the invention.

In some cases, methods of the invention may involve a "one pot" synthesis. That is, the present invention may involve an (at least) three component, one-pot synthesis of N-heterocyclic metallacycle catalysts. The term "one-pot" reaction is known in the art and refers to a chemical reaction which can produce a product in one step which may otherwise have required a multiple-step synthesis, and/or a chemical reaction comprising a series of steps that may be performed in a single reaction vessel. One-pot procedures may eliminate the need for isolation (e.g., purification) of intermediates and additional synthetic steps while reducing the production of waste materials (e.g., solvents, impurities). Additionally, the time and cost required to synthesize such compounds may be reduced. FIG. 1A shows a "one-pot" synthesis of precatalysts, according to one embodiment of the invention.

In one embodiment, the "one pot" synthesis may comprise the simultaneous addition of at least some components of the reaction to a single reaction chamber. In one embodiment, the "one pot" synthesis may comprise sequential addition of various reagents to a single reaction chamber.

Figure 8:
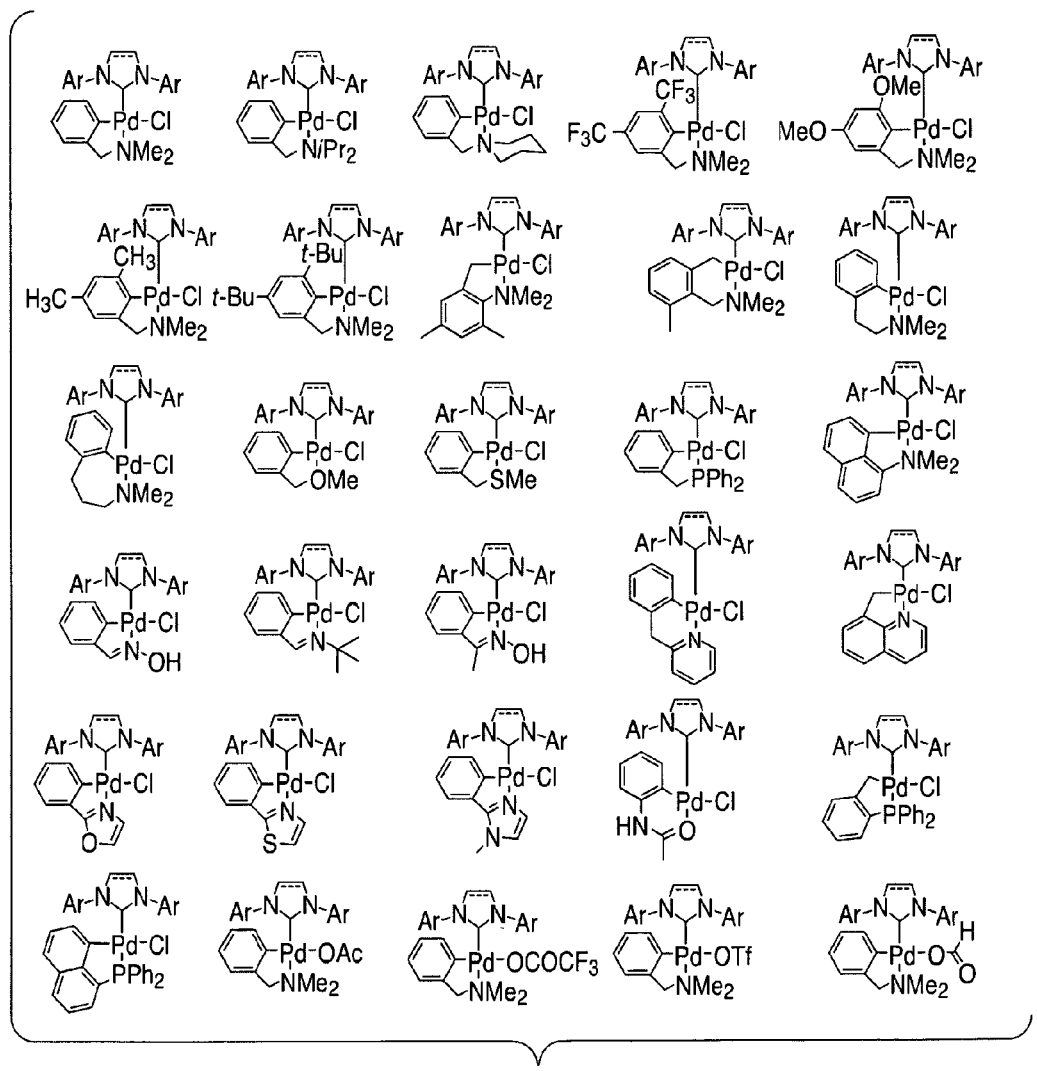
FIG. 8 shows a library of palladium precatalysts, according to some embodiments of the invention.

Methods of the invention may allow for the facile synthesis of libraries of precatalysts. That is, for example, the methods described herein may allow for the combinatorial access to a wide variety of precatalyst frameworks, which may be quickly screened for use as catalysts in cross-coupling reactions. FIG. 8 shows one embodiment of a library of precatalysts that may be synthesized according to the methods described herein. The availability of a wide range of precatalysts may enable the discovery of optimal conditions for a particular cross-coupling reaction, or class of cross-coupling reactions.

As used herein, the term "nucleophile" or "nucleophilic species" is given its ordinary meaning in the art and refers to a chemical moiety having a reactive pair of electrons. Examples of nucleophiles include uncharged compounds such as water, amines, mercaptans and alcohols, and charged moieties such as hydrides, alkoxides, thiolates, carbanions, and a variety of organic and inorganic anions. Organometallic reagents such as organocuprates, organozincs, organolithiums, Grignard reagents, enolates, acetylides, and the like may, under appropriate reaction conditions, may also be suitable nucleophiles. In some cases, the activation agent is a nucleophile such as a hydride, alkoxide, amine, or organometallic reagent. Those of ordinary skill in the art would be capable of selecting an appropriate nucleophile for use as an activating agent.

In some embodiments, metal complexes of the invention may comprise a bidentate ligand which, when bound to a metal center, forms a metallacycle structure with the metal center. Bidentate ligands suitable for use in the present invention include species which have at least two sites capable of binding to a metal center. For example, the bidentate ligand may comprise at least two heteroatoms that coordinate the metal center, or a heteroatom and an anionic carbon atom that coordinate the metal center. The bidentate ligand may also be capable of stabilizing a metal complex comprising an N-heterocyclic carbene ligand. In some embodiments, the bidentate ligand may be chiral and may be provided as a racemic mixture or a purified stereoisomer. Examples of bidentate ligands suitable for use in the invention include, but are not limited to, aryl groups (e.g., bis-aryl, heteroaryl-substituted aryl), heteroaryl groups, alkyl and aryl derivatives of moieties such as amines, phosphines, phosphites, phosphates, imines, oximes, ethers, hybrids thereof, substituted derivatives there of, and the like.

In some embodiments, the bidentate ligand is an aryl group substituted with an amine or alkylamine, wherein coordination to the metal center occurs via a carbon of the aryl group and the nitrogen of the amine group.

Additional ligands may coordinate to the metal center, including neutral ligands and/or charged ligands. Neutral ligands include ligands which may coordinate the metal center but do not alter the oxidation state of the metal center. For example, solvent molecules such as acetonitrile may be neutral ligands. Charged ligands include ligands which may coordinate the metal center and may alter the oxidation state of the metal center. Examples of charged ligands include halides, carboxylates, and the like.

Transition metals suitable for use in the present invention include those which are capable of undergoing oxidative-addition and/or reductive elimination reactions, or other processes associated with cross-coupling reactions. The transition metal may preferably be capable of mediating a cross-coupling reaction to form, for example, carbon-carbon bonds and/or carbon-heteroatom bonds. Transition metals may include transition metals (e.g., Groups 3-12), lathanides, and actinides. In some cases, transition metals from Groups 8-12 are preferred. In some cases, transition metals from Groups 8-10 are preferred. For example, iron, ruthenium, osmium, cobalt, rhodium, iridium, nickel, palladium, and platinum may be preferred. In some embodiments, palladium and ruthenium are preferred.

Various metal-containing compounds may be suitable for use in methods of the invention. In some cases, the metal-containing compound is a palladium-containing compound. The palladium-containing compound may be $PdCl_2$, $Pd(OAc)_2$, $(CH_3CN)_2PdCl_2$, $[Pd(PPh_3)_4]$, or the like.

In some cases, materials of the present invention may comprise N-heterocyclic carbenes, which, without wishing to be bound by theory, may be used as supporting ligands in catalytic processes to enhance the rate and efficiency of the catalytic process and to reduce undesirable side reactions. Examples of N-heterocyclic carbenes include imidazol-2-ylidenes, thiazol-2-ylidenes, dihydroimidazol-2-ylidenes, dihydrothiazol-2-ylidenes, cyclic diaminocarbenes, and other heteroamino carbenes comprising one or more heteroatoms. In some cases, N-heterocyclic carbenes comprising more than two heteroatoms may also be used (e.g., triazol-5-ylidenes).

In some instances, methods of the invention may require additional reagents to promote reactivity of components of the reaction (e.g., metal source, N-heterocyclic carbene salt, bidentate ligand). In particular, it may be advantageous to include a suitable base. For example, the reaction may comprise the insertion (e.g., oxidative addition) of the metal center into a carbon-hydrogen of the bidentate ligand, and the base may serve to deprotonate (e.g., remove the hydrogen) the metal center. The base may also serve to neutralize any acidic species that may be formed during the reaction. In general, a variety of bases may be used in practice of the present invention, such as organic bases and inorganic bases. The base may optionally be sterically hindered to discourage metal coordination of the base in those circumstances where such coordination is possible, i.e., alkali metal alkoxides. Examples of bases include, but are not limited to, alkoxides, alkali metal amides, tertiary amines (e.g. triethylamine, trimethylamine, $Et(i-Pr)_2N$, $Cy_2MeN$, 4-(dimethylamino)pyridine (DMAP), 2,6-lutadine, N-methylpyrrolidine, quinuclidine, and the like), 1,5-diazabicycl[4.3.0]non-5-ene (DBN), 1,5-diazabicyclo[5.4.0]undec-5-ene (DBU), alkali and alkaline earth carbonates (e.g., $Li_2CO_3$, $Na_2CO_3$, $K_2CO_3$, $Cs_2CO_3$, alkali and alkaline earth bicarbonates, alkali and alkaline earth hydroxides, alkali and alkaline earth hydrides, and the like. In some cases, the base is an inorganic base, such as $K_2CO_3$.

Some embodiments of the invention may also require addition of an inorganic salt, including metal halides, metal carbonates and bicarbonates, metal nitrates, metal sulfates, and the like.

In some cases, the solvent may be a polar solvent. Examples of polar solvents include, but are not limited to acetonitrile, DMF, THF, ethylene glycol dimethyl ether (DME), DMSO, acetone, methanol, ethanol, isopropanol, n-propanol, t-butanol or 2-methoxyethyl ether, and the like. In a particular embodiment, the solvent is acetonitrile.

As used herein, the term "reacting" refers to the forming of a bond between two or more components to produce a stable, isolable compound. For example, a first component and a second component may react to form one reaction product comprising the first component and the second component joined by a covalent bond. That is, the term "reacting" does not refer to the interaction of solvents, catalysts, bases, ligands, or other materials which may serve to promote the occurrence of the reaction with the component(s). A "stable compound" or "isolable compound" refers to an isolated reaction product and does not refer to unstable intermediates or transition states.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

EXAMPLES

Example 1

Figure 3B:
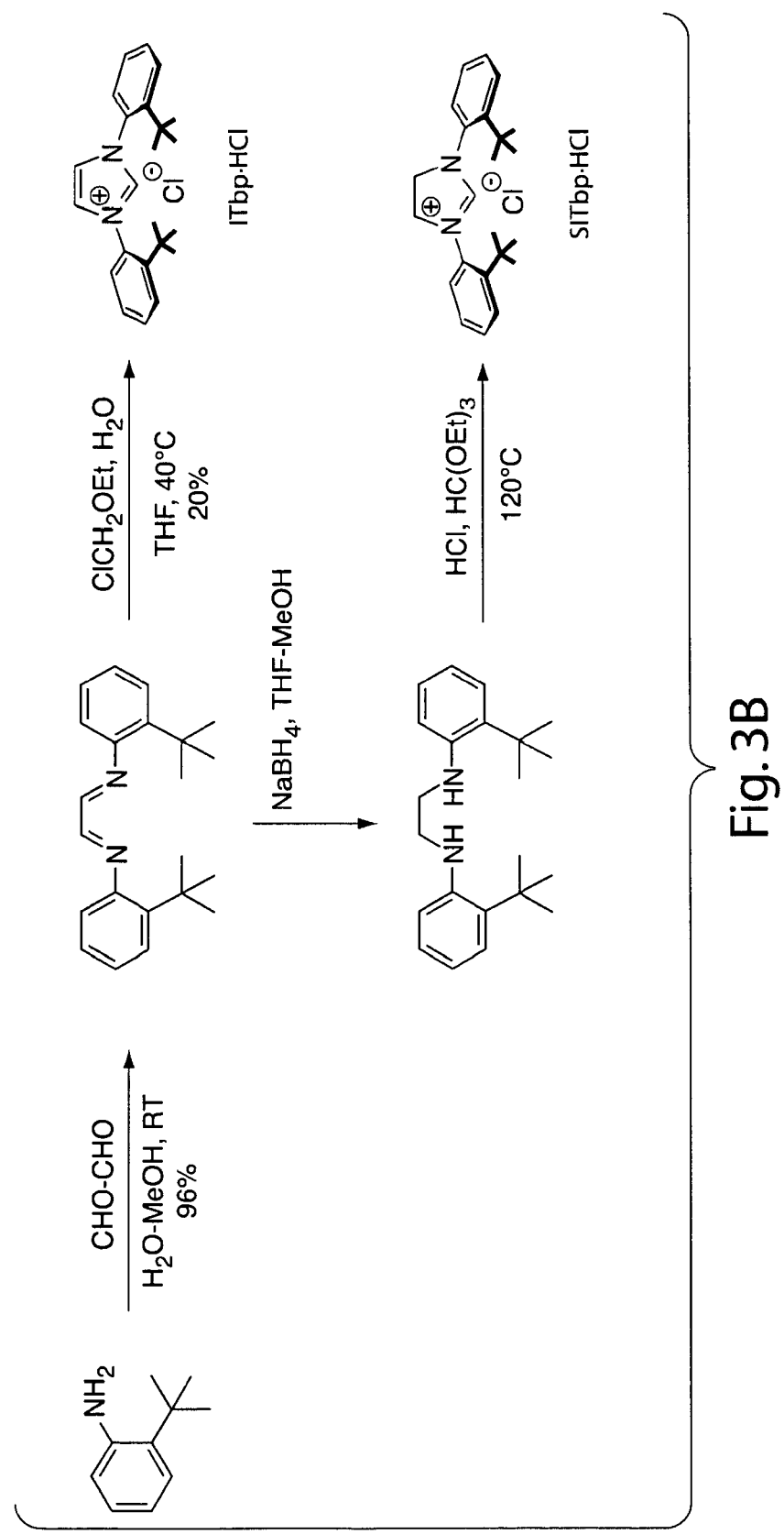
FIG. 3B shows the synthesis of N-heterocyclic carbene ligand precursors, according to some embodiments of the invention.
Figure 3C:
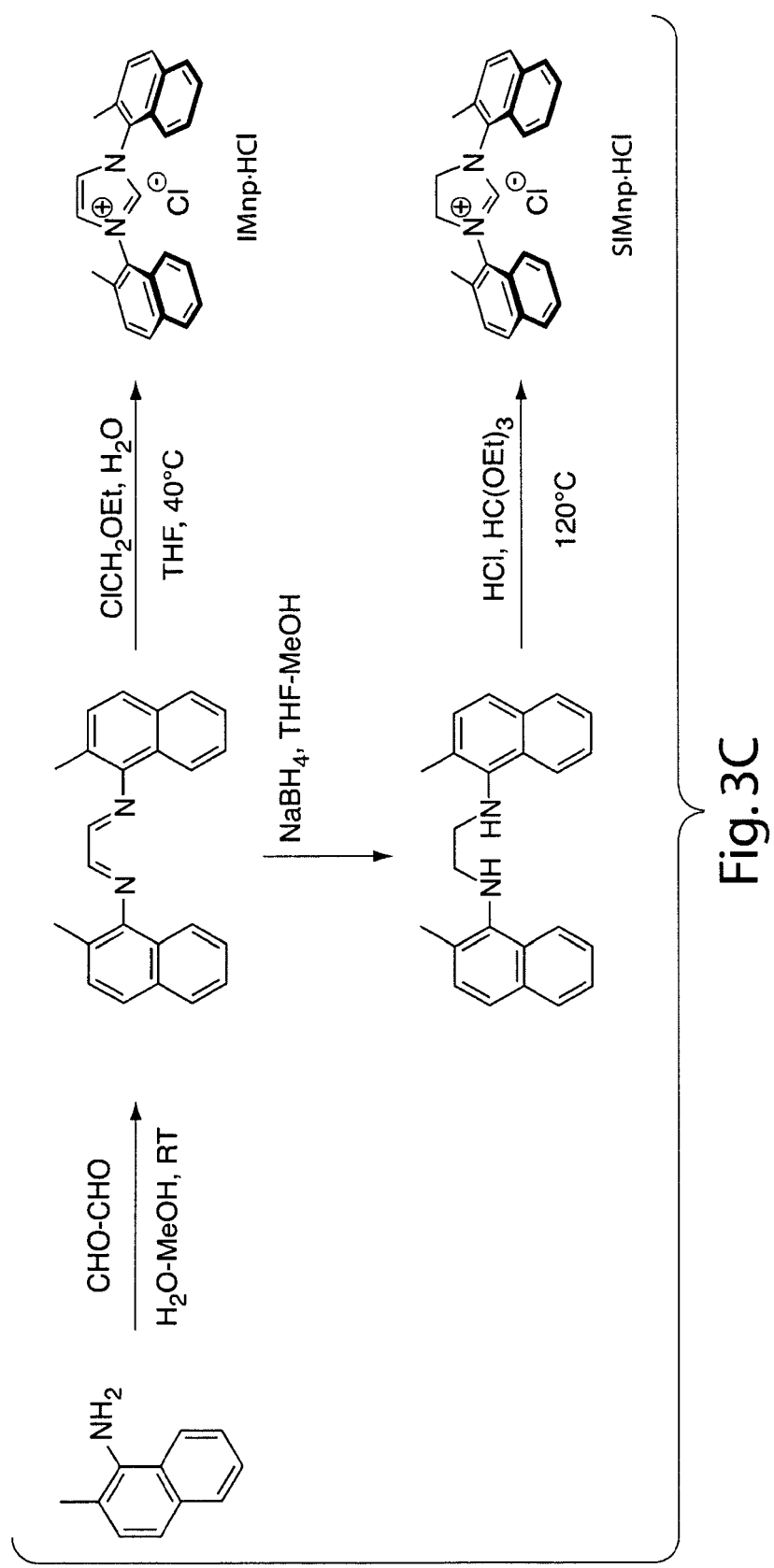
FIG. 3C shows the synthesis of N-heterocyclic carbene ligand precursors, according to some embodiments of the invention.

FIG. 3B shows a schematic synthesis of compound ITb-p.HCl, which was synthesized according to the following method. To a solution of 2-tert-butylaniline (20.4 mL, 19.6 g, 131 mmol) in mixture of methanol (50 mL) and water (5 mL), a glyoxal solution (40% in water; 7.5 mL, 9.43 g, 65 mmol) was added, and the mixture stirred over 1.5 h. The yellow crystalline mass of the diazabutadiene intermediate was filtered off, dried with a stream of air, and then vacuum-dried over $P_2O_5$. The diazabutadiene was obtained as yellow powder (19.91 g, 96%) and used directly for the next step.

To a solution of the diazabutadiene (6.41 g, 20 mmol) in THF (40 mL), chloromethyl ethyl ether (2.0 mL, 2.08 g, 22 mmol) and water (0.4 mL) were added in succession and the mixture was stirred at 40° C. over 18 h. The solvent was removed and the residue was partitioned between ethyl acetate (50 mL) and water (50 mL). The organic layer was further extracted with water (2×25 mL). The combined aqueous layers were then extracted with $CH_2Cl_2$ (4×25 mL). The combined $CH_2Cl_2$ layers were dried over $MgSO_4$), and the solvent was removed under reduced pressure. The residue was triturated with $CHCl_3$-ethyl acetate (1:5). The imidazolium salt, ITBp.HCl (1.45 g, 20%), was obtained as an off-white solid. $^1H$ NMR ($CD_2Cl_2$, 400 MHz): δ 11.7-9.7 (broad s, 1H); 8.4-6.7 (broad s, 2H), 7.74 (m, 2H), 7.62 (td, J=8.8, 1.6 Hz, 2H); 7.45 (td, J=7.6, 1.2 Hz, 2H), 1.36 (s, 9H). $^{13}C$ NMR ($CD_2Cl_2$, 100 MHz): δ 145.9 (broad), 140.9 (broad), 131.7, 129.1 (broad), 127.6, 125.6 (broad), 356.0, 31.8. Anal Calcd. For $C_{23}H_{29}ClN_3$ (368.94): C, 74.88; H, 7.92; N, 7.59. Found: C, 75.05, 7.89, 7.72.

Example 2

Figure 4A:
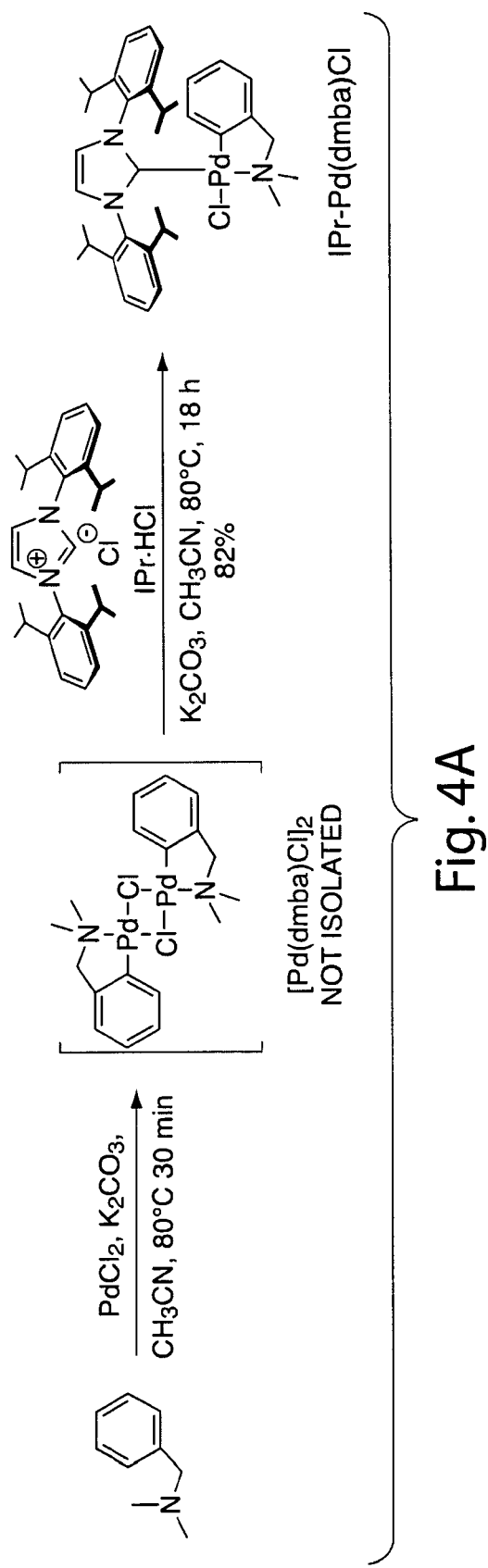
FIGS. 4A-J show the syntheses of various precatalysts, according to some embodiments of the invention.

FIG. 4A shows a schematic synthesis of IPr—Pd(dmba)Cl (dmba=$k^2$N,C—N,N-dimethylbenzylamine), which was synthesized according to the following method. Finely powdered $PdCl_2$ (177 mg, 1.00 mmol) was suspended in $CH_3CN$ (5 mL), and N-benzyldimethylamine (160 μL, 143 mg, 1.05 mmol) were added. The solution was heated to 80° C. with stirring a until clear, orange solution was formed (approx. 20 min). Finely powdered $K_2CO_3$ (691 mg, 5.00 mmol) was added and the stirring was continued until palladacycle formation was complete, as indicated by the formation of a canary yellow solution (5-10 min). IPr.HCl (467 mg, 1.10 mmol) was added and the mixture was stirred at 80° C. over 18 h. The reaction mixture was filtered and evaporated. The resulting product was purified by column chromatography. Upon application of the product to a pad of silica gel (2.5×8 cm) pre-equilibrated with $CH_2Cl_2$, $CH_2Cl_2$ (100 mL) was used to elute impurities. The pure NHC-palladacycles were eluted with $CH_2Cl_2$-ethylacetate (3:1, vol/vol, 150 mL), and the solvents were evaporated. The products were triturated with hexanes (25 mL). After drying in high vacuum, IPr—Pd (dmba)Cl (543 mg, 82%) was obtained as beige solid. $^1H$ NMR (CDCl$_3$, 400 MHz) δ: 7.40 (t, J=7.6 Hz, 2H), 7.30 (d, J=7.6 Hz, 2H); 7.21 (s, 2H), 6.82-6.70 (m, 3H), 6.53 (d, J=7.6 Hz, 1H), 3.46 (s, 2H), 3.37 (m, 2H), 3.15 (m, 2H), 2.39 (s, 6H), 1.49 (d, J=6.8 Hz, 6H), 1.18 (d, J=6.8 Hz, 6H), 1.02 (d, J=6.8 Hz, 6H), 0.81 (d, J=6.4 Hz, 6H). $^{13}$C NMR (CDCl$_3$, 100 MHz) δ: 177.5, 150.5, 147.8, 147.8, 144.7, 136.2, 136.1, 129.7, 125.4, 124.6, 124.0, 123.8, 122.6, 121.5, 72.6, 49.8, 29.0, 28.3, 26.4, 26.2, 23.2, 23.2. Anal. calcd for C$_{36}$H$_{48}$ClN$_3$Pd (665.67): C, 65.05; H, 7.28; N, 6.32. Found: C, 65.14; H, 7.41; N, 6.53.

Example 3

Figure 4B:
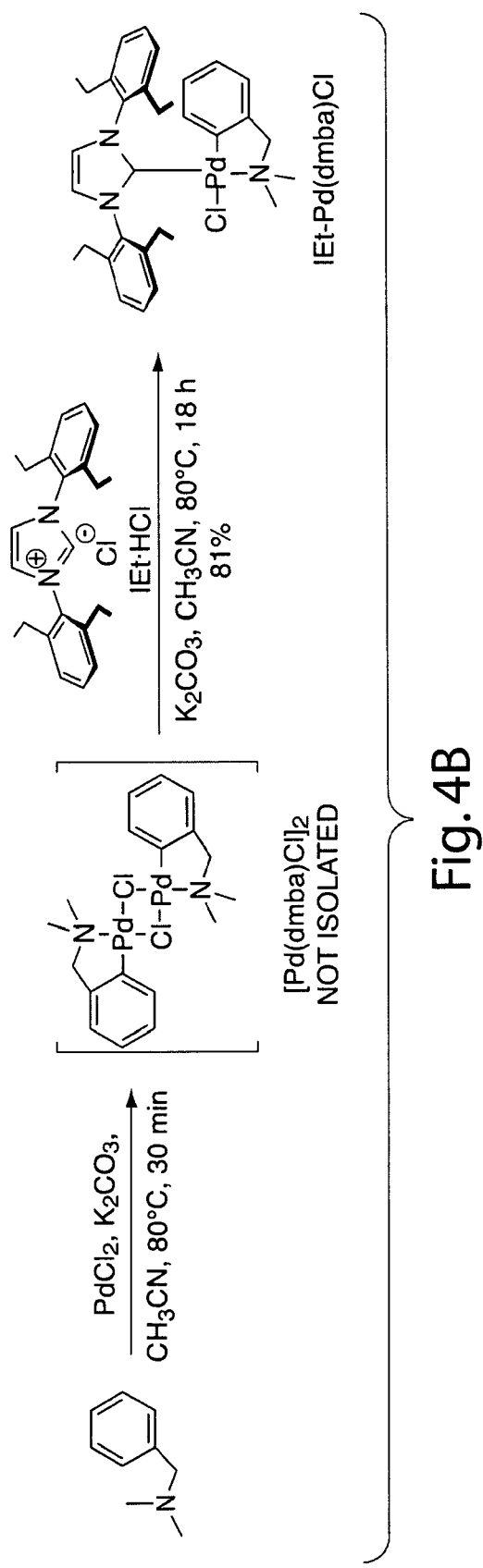

FIG. 4B shows a schematic synthesis of IEt-Pd(dmba)Cl, which was synthesized according to the following method. Finely powdered PdCl$_2$ (177 mg, 1.00 mmol) was suspended in CH$_3$CN (5 mL) and N-benzyldimethylamine (160 μL, 143 mg, 1.05 mmol) were added. The solution was heated to 80° C. with stirring until a clear, orange solution was formed (approx. 20 min). Finely powdered K$_2$CO$_3$ (691 mg, 5.00 mmol) was added and the stirring was continued until palladacycle formation was complete, as indicated by the formation of a canary yellow solution (5-10 min). IEt.HCl (406 mg, 1.10 mmol) was added and the mixture was stirred at 80° C. over 18 h. The reaction mixture was filtered and evaporated. The resulting product was purified by column chromatography. Upon application of the product to a pad of silica gel (2.5×8 cm) pre-equilibrated with CH$_2$Cl$_2$, CH$_2$Cl$_2$ (100 mL) was used to elute impurities. The pure NHC-palladacycles were eluted with CH$_2$Cl$_2$-ethylacetate (3:1, vol/vol, 150 mL), and the solvents were evaporated. The products triturated with hexanes (25 mL). After drying in high vacuum, IEt-Pd(dmba)Cl (492 mg, 81%) was obtained as beige solid. $^1$H NMR (CDCl$_3$, 400 MHz) δ: 7.30 (t, J=7.6 Hz, 2H), 7.24 (dd, J=7.6, 1.2 Hz, 2H), 7.16 (s, 2H), 7.04 (dd, J=7.6, 1.2 Hz, 2H), 6.78 (td, J=7.6, 1.2 Hz, 1H), 6.71 (d, J=7.2, 1.0 Hz, 1H), 6.68 (td, J=7.6, 1.2 Hz, 1H), 6.58 (d, J=7.2, 1.0 Hz, 1H), 3.44 (s, 2H), 2.94 (m, 2H), 2.87 (m, 2H), 2.70 (m, 2H), 2.61 (m, 2H), 2.40 (s, 6H), 1.19 (t, J=7.2 Hz, 6H), 1.18 (d, J=7.6 Hz, 6H). $^{13}$C NMR (CDCl$_3$, 100 MHz) δ: 175.7, 150.0, 147.2, 143.1, 137.0, 137.3, 137.1, 129.1, 126.3, 126.0, 124.0, 123.4, 122.7, 121.1, 72.3, 50.0, 29.0, 25.9, 25.2, 13.3, 14.7. Anal. calcd for C$_{32}$H$_{41}$ClN$_3$Pd (609.56): C, 63.16; H, 6.63; N, 6.90. Found: C, 63.69; H, 6.80; N, 7.03.

Example 4

Figure 4C:
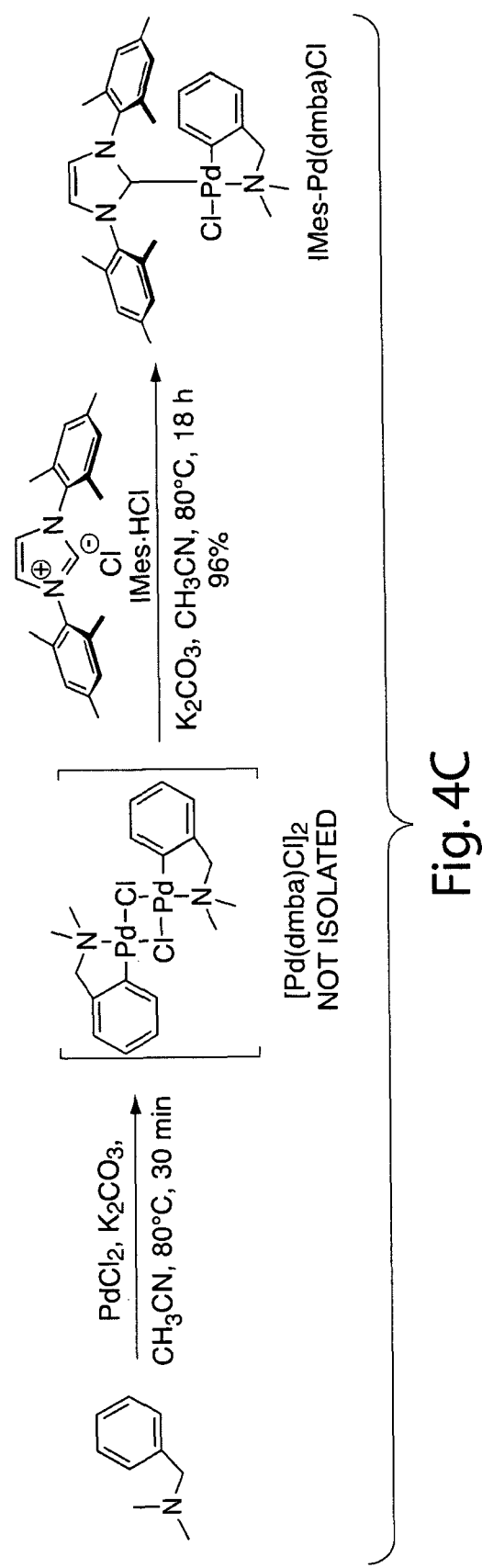

FIG. 4C shows a schematic synthesis of IMes-Pd(dmba)Cl, which was synthesized according to the following method. Finely powdered PdCl$_2$ (177 mg, 1.00 mmol) was suspended in CH$_3$CN (5 mL) and N-benzyldimethylamine (160 μL, 143 mg, 1.05 mmol) were added. The solution was heated to 80° C. with stirring until a clear, orange solution was formed (approx. 20 min). Finely powdered K$_2$CO$_3$ (691 mg, 5.00 mmol) was added and the stirring was continued until palladacycle formation was complete, as indicated by the formation of a canary yellow solution (5-10 min). IMes.HCl (375 mg, 1.10 mmol) was added and the mixture was stirred at 80° C. over 18 h. The reaction mixture was filtered and evaporated. The resulting product was purified by column chromatography. Upon application of the product to a pad of silica gel (2.5×8 cm) pre-equilibrated with CH$_2$Cl$_2$, CH$_2$Cl$_2$ (100 mL) was used to elute impurities. The pure NHC-palladacycles were eluted with CH$_2$Cl$_2$-ethylacetate (3:1, vol/vol, 150 mL), and the solvent was evaporated. The products were triturated with hexanes (25 mL). After drying in high vacuum, IMes-Pd(dmba)Cl (555 mg, 96%) was obtained as beige solid. $^1$H NMR (CDCl$_3$, 400 MHz) δ: 7.10 (s, 2H), 6.99 (s, 2H), 6.83-6.76 (m, 4H), 6.70 (td, J=7.6, 1.2 Hz, 1H), 6.58 (d, J=7.2, 1.2 Hz, 1H), 3.53 (s, 2H), 2.45 (s, 6H), 2.44 (s, 6H), 2.29 (s, 6H), 2.23 (s, 6H). $^{13}$C NMR (CDCl$_3$, 100 MHz) δ: 175.6, 149.3, 147.6, 138.3, 138.3, 137.4, 136.2, 133.9, 129.4, 128.7, 123.9, 123.2, 123.0, 121.2, 72.2, 50.0, 21.1, 20.2, 19.8. Anal. calcd for C$_{30}$H$_{37}$ClN$_3$Pd (581.51): C, 61.96; H, 6.41; N, 7.23. Found: C, 62.02; H, 6.37; N, 7.40.

Example 5

Figure 4D:
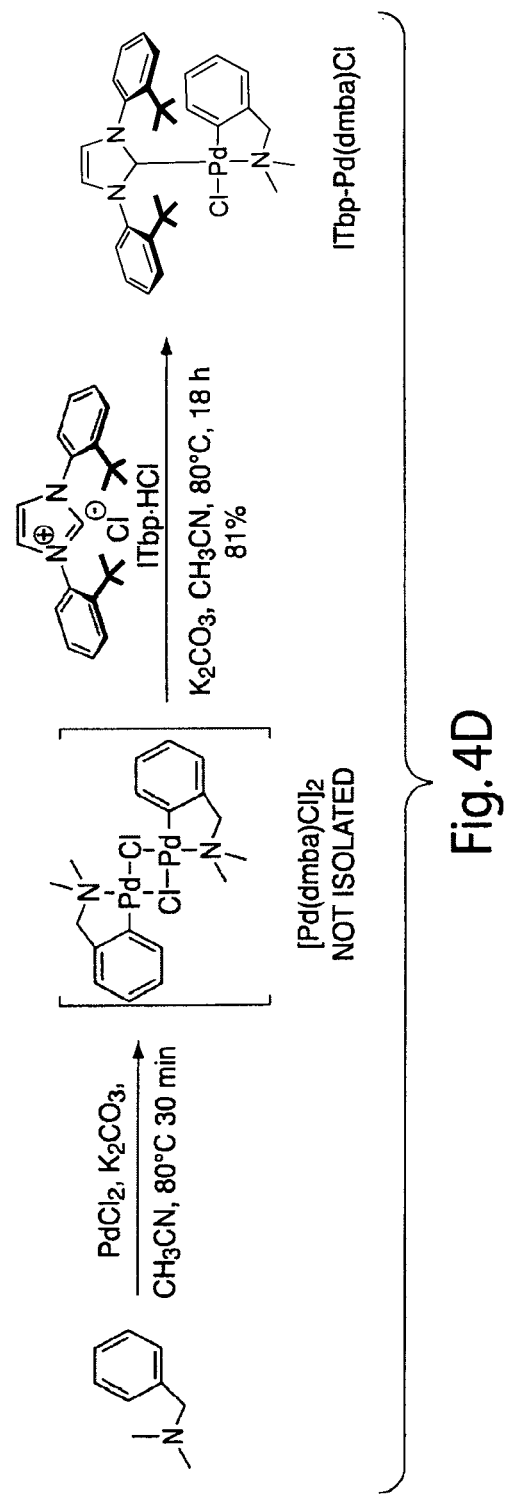

FIG. 4D shows a schematic synthesis of ITbp-Pd(dmba)Cl, which was synthesized according to the following method. Finely powdered PdCl$_2$ (177 mg, 1.00 mmol) was suspended in CH$_3$CN (5 mL) and N-benzyldimethylamine (160 μL, 143 mg, 1.05 mmol) were added. The solution was heated to 80° C. with stirring until a clear, orange solution was formed (approx. 20 min). Finely powdered K$_2$CO$_3$ (691 mg, 5.00 mmol) was added and the stirring was continued until the palladacycle formation was complete, as indicated by the formation of a canary yellow solution (5-10 min). ITbp.HCl (406 mg, 1.10 mmol) was added and the mixture was stirred at 80° C. over 18 h. The reaction mixture was filtered and evaporated. The resulting product was purified by column chromatography. Upon application of the product to a pad of silica gel (2.5×8 cm) pre-equilibrated with CH$_2$Cl$_2$, CH$_2$Cl$_2$ (100 mL) was used to elute impurities. The pure NHC-palladacycles were eluted with CH$_2$Cl$_2$-ethylacetate (3:1, vol/vol, 150 mL) and the solvents were evaporated. The products were triturated with hexanes (25 mL). After drying in high vacuum, ITbp-Pd(dmba)Cl (494 mg, 81%) was obtained as beige solid. $^1$H NMR (CDCl$_3$, 400 MHz) δ: 7.62 (dd, J=8.4, 1.6 Hz, 2H), 7.42 (dd, J=8.0, 1.2 Hz, 2H), 7.30-7.22 (m, 2H), 7.29 (s, 2H), 6.93-6.81 (m, 5H), 6.39 (d, J=7.2 Hz), 3.51 (s, 2H), 2.42 (s, 6H); 1.51 (s, 18H). $^{13}$C NMR (CDCl$_3$, 100 MHz) δ: 176.7, 151.8, 148.0, 146.7, 137.6, 137.5, 131.8, 129.8, 128.7, 125.1, 125.1, 124.7, 123.0, 121.6, 72.4, 49.6, 36.7, 32.8. Anal. calcd for C$_{32}$H$_{41}$ClN$_3$Pd (609.56): C, 63.05; H, 6.78; N, 6.89. Found: C, 63.69; H, 6.81; N, 7.11.

Example 6

Figure 4E:
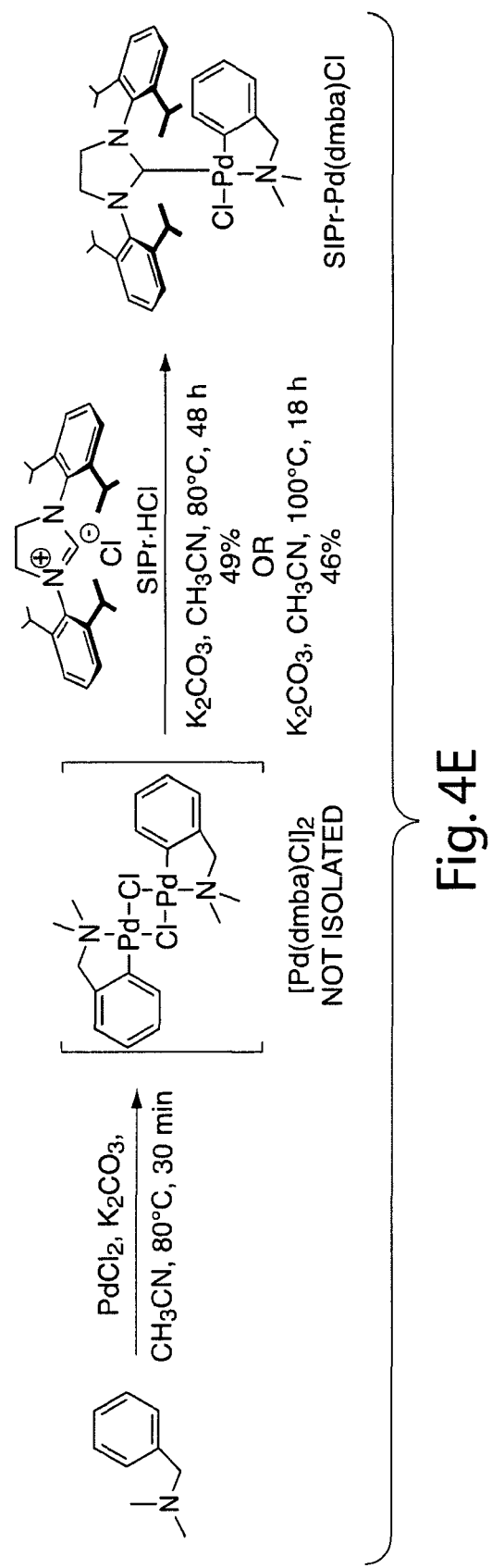

FIG. 4E shows a schematic synthesis of SIPr—Pd(dmba)Cl (dmba=k$^2$N,C—N,N-dimethylbenzylamine), which was synthesized according to the following method. Finely powdered PdCl$_2$ (177 mg, 1.00 mmol) was suspended in CH$_3$CN (5 mL) and N-benzyldimethylamine (160 μL, 143 mg, 1.05 mmol) were added. The solution was heated to 80° C. with stirring until a clear, orange solution was formed (approx. 20 min). Finely powdered K$_2$CO$_3$ (691 mg, 5.00 mmol) was added and the stirring was continued until palladacycle formation was complete, as indicated by the formation of a canary yellow solution (5-10 min). SIPr.HCl (469 mg, 1.10 mmol) was added and the mixture was stirred at 80° C. over 48 h. Alternatively, the mixture was heated at 100° C. over 18 h. The reaction mixture was filtered and evaporated. The resulting product was purified by column chromatography. Upon application of the product to a pad of silica gel (2.5×8 cm) pre-equilibrated with CH$_2$Cl$_2$, CH$_2$Cl$_2$ (100 mL) was used to elute impurities. The pure NHC-palladacycles were eluted with CH$_2$Cl$_2$-ethylacetate (3:1, vol/vol, 150 mL) and the solvents were evaporated. The products were triturated with hexanes (25 mL). After drying in high vacuum, SIPr—Pd(dmba)Cl (328 mg, 49% at 80° C. and 308 mg, 46% at 100° C.) was obtained as beige solid. $^1$H NMR (CDCl$_3$, 400 MHz) δ: 7.36-7.28 (m, 4H), 7.22 (m, 1H); 7.10 (dd, J=7.2, 1.6 Hz, 2H), 6.85 (m, 3H), 6.78 (m, 1H), 4.16 (m, 2H), 4.10 (m, 2H), 3.59 (m, 4H), 3.40 (s, 2H), 2.32 (s, 6H), 1.60 (d, J=6.8 Hz, 6H), 1.26 (d, J=6.8 Hz, 6H), 1.21 (d, J=6.8 Hz, 6H), 0.74 (d, J=6.8 Hz, 6H). $^{13}$C NMR (CDCl$_3$, 100 MHz) δ: 205.4, 150.7, 148.0, 147.9, 146.3, 136.9, 136.0, 128.8, 125.3, 124.4, 124.0, 122.8, 121.7, 72.6, 54.2, 49.5, 29.0, 28.4, 27.0, 26.3, 24.3, 23.6. Anal. calcd for C$_{36}$H$_{50}$ClN$_3$Pd (666.68): C, 64.86; H, 7.56; N, 6.30. Found: C, 65.19; H, 7.76; N, 6.39.

Example 7

Figure 4F:
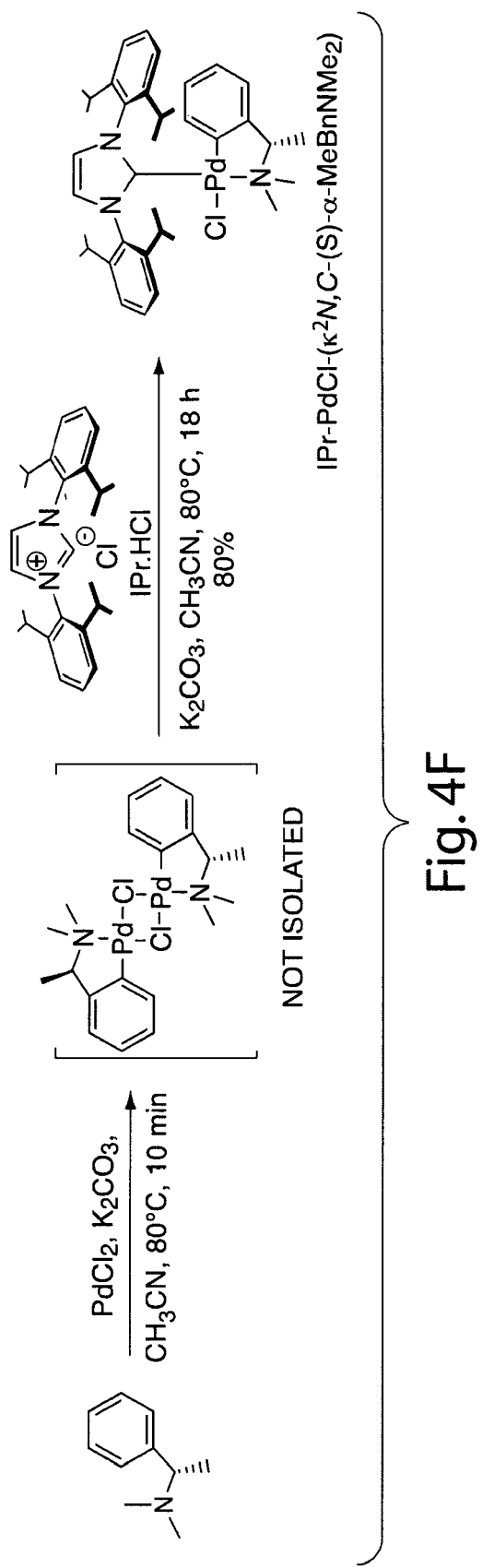

FIG. 4F shows a schematic synthesis of IPr—PdCl-(k$^2$N, C—(S)-α-MeBnNMe$_2$), which was synthesized according to the following method. Finely powdered (CH$_3$CN)$_2$PdCl$_2$ (259 mg, 1.00 mmol) was suspended in CH$_3$CN (5 mL) and (S)-α,N,N-trimethylbenzylamine (173 μL, 157 mg, 1.05 mmol) was added. The solution was heated to 80° C. for 5 min and finely powdered K$_2$CO$_3$ (691 mg, 5.00 mmol) was added. The stirring was continued until palladacycle formation was complete, as indicated by the formation of a canary yellow solution (5-10 min). IPr.HCl (467 mg, 1.10 mmol) was added and the mixture was stirred at 80° C. over 18 h. The reaction mixture was filtered and evaporated. The resulting product was purified by column chromatography. Upon application of the product to a pad of silica gel (2.5×8 cm) pre-equilibrated with CH$_2$Cl$_2$, CH$_2$Cl$_2$ (100 mL) was used to elute impurities. The pure NHC-palladacycles were eluted with CH$_2$Cl$_2$-ethylacetate (3:1, vol/vol, 150 mL), and the solvents were evaporated. The products were triturated with hexanes (25 mL). After drying in high vacuum, IPr—PdCl-(k$^2$N,C—(S)-a-MeBnNMe$_2$) (542 mg, 80%) was obtained as beige solid. $^1$H NMR (CDCl$_3$, 400 MHz) δ: 7.46 (t, J=8.0 Hz, 2H), 7.34 (d, J=4.4 Hz, 2H); 7.30-7.25 (m, 3H), 7.24 (d, J=1.6 Hz, 1H); 7.19 (d, J=1.6 Hz), 7.04 (m, 1H), 6.80 (td, J=7.2, 1.2 Hz, 1H), 6.74 (m, 1H), 6.70 (dd, J=7.2, 2.0 Hz, 1H), 6.55 (d, J=6.8 Hz, 1H), 3.81 (m, 1H), 3.67 (m, 1H), 3.10 (q, J=6.4 Hz, 1H), 2.92 (m, 1H), 2.45 (m, 1H), 2.37 (s, 3H), 2.27 (s, 3H), 1.52 (d, J=6.8 Hz, 3H), 1.44 (d, J=6.8 Hz, 3H), 1.20 (d, J=6.8 Hz, 3H), 1.17 (d, J=5.6 Hz, 3H), 1.15 (d, J=5.6 Hz, 3H), 1.08 (d, J=6.8 Hz, 3H), 0.96 (d, J=6.4 Hz, 3H), 0.90 (d, J=6.8 Hz, 3H), 0.46 (d, J=6.4 Hz, 3H). $^{13}$C NMR (CDCl$_3$, 100 MHz) δ: 178.0, 154.5, 149.4, 147.9, 147.6, 144.8, 144.7, 136.5, 136.1, 136.0, 129.8, 129.5, 125.2, 125.2, 124.1, 123.8, 123.7, 122.7, 121.1, 75.3, 50.0, 46.6, 29.0, 29.0, 28.4, 28.2, 27.0, 26.8, 26.0, 25.3, 23.6, 23.4, 22.8, 22.6.

Example 8

Figure 4G:
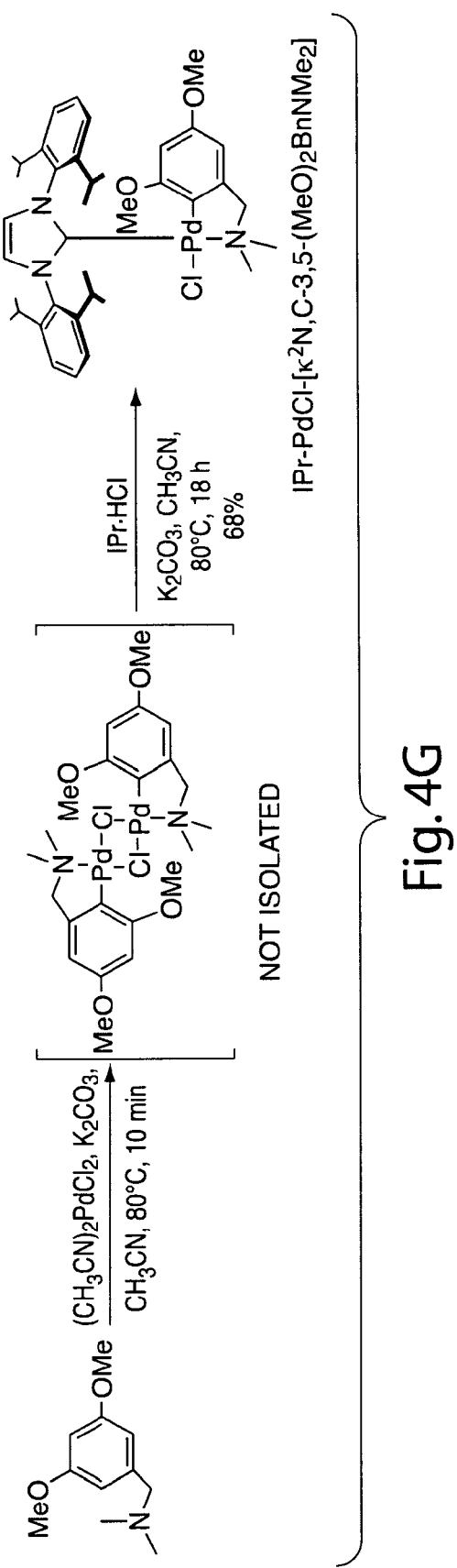

FIG. 4G shows a schematic synthesis of IPr—PdCl-[k$^2$N, C-3,5-(MeO)$_2$BnNMe$_2$], which was synthesized according to the following method. Finely powdered (CH$_3$CN)$_2$PdCl$_2$ (259 mg, 1.00 mmol) was suspended in CH$_3$CN (5 mL) and 3,5-dimetoxy-N,N-dimethylbenzylamine (205 mg, 1.05 mmol) was added. The solution was heated to 80° C. for 5 min and finely powdered K$_2$CO$_3$ (691 mg, 5.00 mmol) was added. The stirring was continued until palladacycle formation was complete, as indicated by the formation of a canary yellow solution (5-10 min). IPr.HCl (467 mg, 1.10 mmol) was added and the mixture stirred at 80° C. over 18 h. The reaction mixture was filtered and evaporated. The resulting product was purified by column chromatography. Upon application of the product to a pad of silica gel (2.5×8 cm) pre-equilibrated with CH$_2$Cl$_2$, CH$_2$Cl$_2$ (100 mL) was used to elute impurities. The pure NHC-palladacycles were eluted with CH$_2$Cl$_2$-ethylacetate (3:1, vol/vol, 150 mL) and the solvents were evaporated. The products triturated with hexanes (25 mL). After drying in high vacuum, IPr—PdCl-[k$^2$N,C-3,5-(MeO)$_2$Bn-NMe$_2$] (491 mg, 68%) was obtained as yellow solid. $^1$H NMR (CDCl$_3$, 400 MHz) δ: 7.39 (t, J=7.6 Hz, 2H), 7.27 (dd, J=7.6, 1.6 Hz, 2H), 7.18 (dd, J=7.6, 1.2 Hz, 2H), 7.13 (s, 2H), 6.12 (d, J=2.4 Hz, 3H), 5.99 (d, J=2.4 Hz, 3H), 3.71 (s, 3H), 3.69 (m, 2H), 3.49 (s, 3H), 3.33 (s, 2H), 2.94 (m, 2H), 2.33 (s, 6H), 1.47 (d, J=6.4 Hz, 6H), 1.18 (d, J=6.8 Hz, 6H), 1.03 (d, J=7.2 Hz, 6H), 0.99 (d, J=6.4 Hz, 6H). $^{13}$C NMR (CDCl$_3$, 100 MHz) δ: 175.5, 161.8, 157.4, 149.1, 148.2, 145.4, 136.8, 129.3, 127.9, 123.8, 123.7, 123.7, 99.9, 95.2, 73.4, 55.1, 54.9, 49.6, 29.0, 27.0, 26.6, 26.5, 24.2, 23.4.

Example 9

Figure 4H:
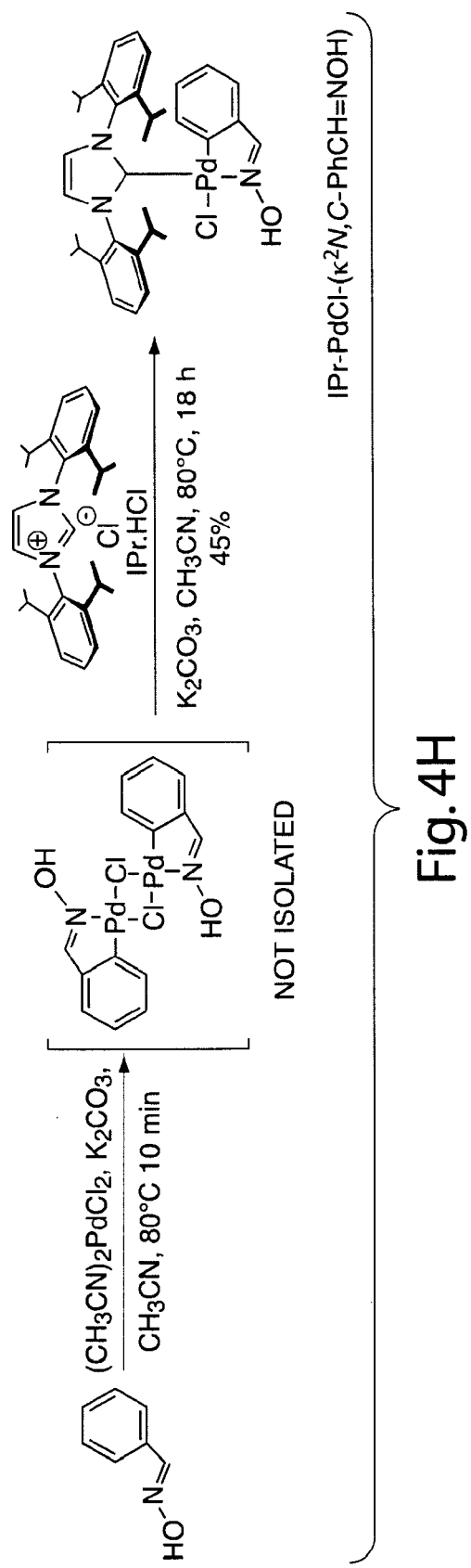

FIG. 4H shows a schematic synthesis of IPr—PdCl-[k$^2$N, C-PhCH═NOH], which was synthesized according to the following method. Finely powdered (CH$_3$CN)$_2$PdCl$_2$ (259 mg, 1.00 mmol) was suspended in CH$_3$CN (5 mL) and (E)-benzaldehyde oxime (127 mg, 1.05 mmol) were added. The solution was heated to 80° C. for 5 min and finely powdered K$_2$CO$_3$ (691 mg, 5.00 mmol) was added and the stirring continued until palladacycle formation was complete, as indicated by the formation of a canary yellow solution (5-10 min). IPr.HCl (467 mg, 1.10 mmol) was added and the mixture stirred at 80° C. over 18 h. The reaction mixture was filtered and evaporated. The resulting product was purified by column chromatography. Upon application of the product to a pad of silica gel (2.5×8 cm) pre-equilibrated with CH$_2$Cl$_2$, CH$_2$Cl$_2$ (100 mL) was used to elute impurities. The pure NHC-palladacycles were eluted with CH$_2$Cl$_2$-ethylacetate (1:1, vol/vol, 150 mL) and the solvents were evaporated. The products were triturated with hexanes (25 mL). After drying in high vacuum, IPr—PdCl-[k$^2$N,C-PhCH═NOH] (291 mg, 45%) was obtained as yellow solid. $^1$H NMR (CDCl$_3$, 400 MHz) δ: 7.40 (t, J=8.0 Hz, 2H), 7.24 (dd, J=8.0, 1.6 Hz, 2H), 7.18 (dd, J=7.6, 1.2 Hz, 2H), 7.15 (s, 1H), 7.13 (s, 2H), 6.72 (dd, J=7.2, 1.2 Hz, 1H), 6.68 (td, J=8.4, 1.2 Hz, 1H), 6.46 (d, J=6.4 Hz, 3H), 6.42 (td, J=6.4, 1.6 Hz, 3H), 3.43 (s, 2H), 3.00 (s, 2H), 1.74 (broad s, 1H), 1.14 (d, J=7.2 Hz, 6H), 1.11 (d, J=6.8 Hz, 6H), 0.95 (d, J=6.4 Hz, 6H), 0.90 (d, J=6.8 Hz, 6H). $^{13}$C NMR (CDCl$_3$, 100 MHz) δ: 182.0, 154.2, 152.0, 146.8, 146.0, 145.2, 137.0, 136.1, 129.3, 124.5, 123.9, 123.8, 123.2, 122.2, 121.0, 28.6, 28.0, 26.3, 26.0, 23.9, 22.4.

Example 10

Figure 4I:
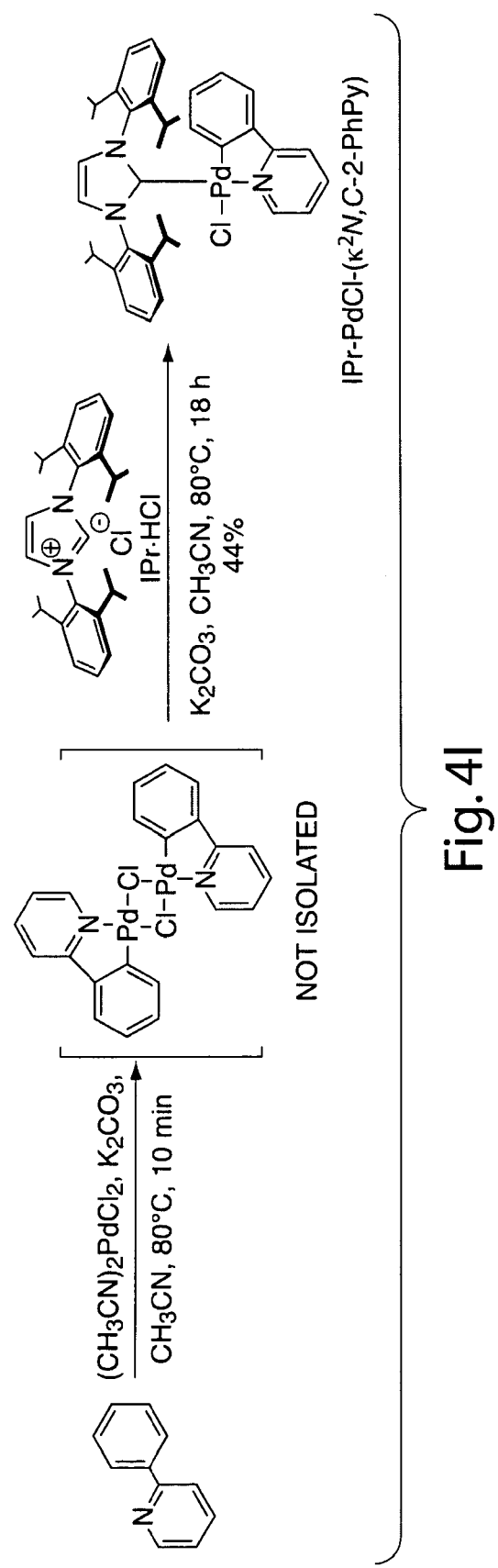

FIG. 4I shows a schematic synthesis of IPr—PdCl-[k$^2$N, C-2-PhPy], which was synthesized according to the following method. Finely powdered (CH$_3$CN)$_2$PdCl$_2$ (259 mg, 1.00 mmol) was suspended in CH$_3$CN (5 mL) and 2-phenylpyridine (150 μL, 163 mg, 1.05 mmol) was added. The solution was heated to 80° C. for 5 min and finely powdered K$_2$CO$_3$ (691 mg, 5.00 mmol) was added. The stirring was continued until palladacycle formation was complete, as indicated by the formation of a canary yellow solution (5-10 min). IPr.HCl (467 mg, 1.10 mmol) was added and the mixture was stirred at 80° C. over 18 h. The reaction mixture was filtered and evaporated. The resulting product was purified by column chromatography. Upon application of the product to a pad of silica gel (2.5×8 cm) pre-equilibrated with CH$_2$Cl$_2$, CH$_2$Cl$_2$ (100 mL) was used to elute impurities. The pure NHC-palladacycles were eluted with CH$_2$Cl$_2$-ethylacetate (1:1, vol/vol, 150 mL) and the solvents were evaporated. The products were triturated with hexanes (25 mL). After drying in high vacuum, IPr—PdCl-[k$^2$N,C-2-PhPy] (300 mg, 44%) was obtained as yellow solid. $^1$H NMR (CDCl$_3$, 400 MHz) δ: 9.30 (d, J=0.8 Hz, 1H), 7.57 (td, J=8.0, 1.6 Hz, 1H), 7.45 (d, J=8.4 Hz, 1H), 7.38 (t, J=8.0 Hz, 2H), 7.33 (dd, J=8.0, 1.6 Hz, 2H), 7.30 (dd, J=7.6, 1.6 Hz, 1H), 7.28 (s, 2H), 7.18 (dd, J=7.6, 1.6 Hz, 2H), 6.96 (td, J=7.6, 1.2 Hz, 1H), 6.93 (dd, J=7.6, 1.6 Hz, 1H), 6.89 (td, J=7.6, 1.6 Hz, 3H), 6.73 (dd, J=7.2, 0.8 Hz, 3H), 3.36 (m, 2H), 3.30 (m, 2H), 1.50 (d, J=6.4 Hz, 6H), 1.18 (d, J=6.8 Hz, 6H), 1.05 (d, J=6.8 Hz, 6H), 0.80 (d, J=6.8 Hz, 6H). $^{13}$C NMR (CDCl$_3$, 100 MHz) δ: 178.8, 164.3, 155.7, 150.1, 147.8, 146.4, 145.0, 137.8, 137.5, 135.9, 129.9, 128.9, 125.0, 124.2, 124.0, 123.1, 122.8, 121.4, 117.4, 29.0, 28.5, 26.6, 26.2, 23.2, 22.0.

Example 11

Figure 4J:
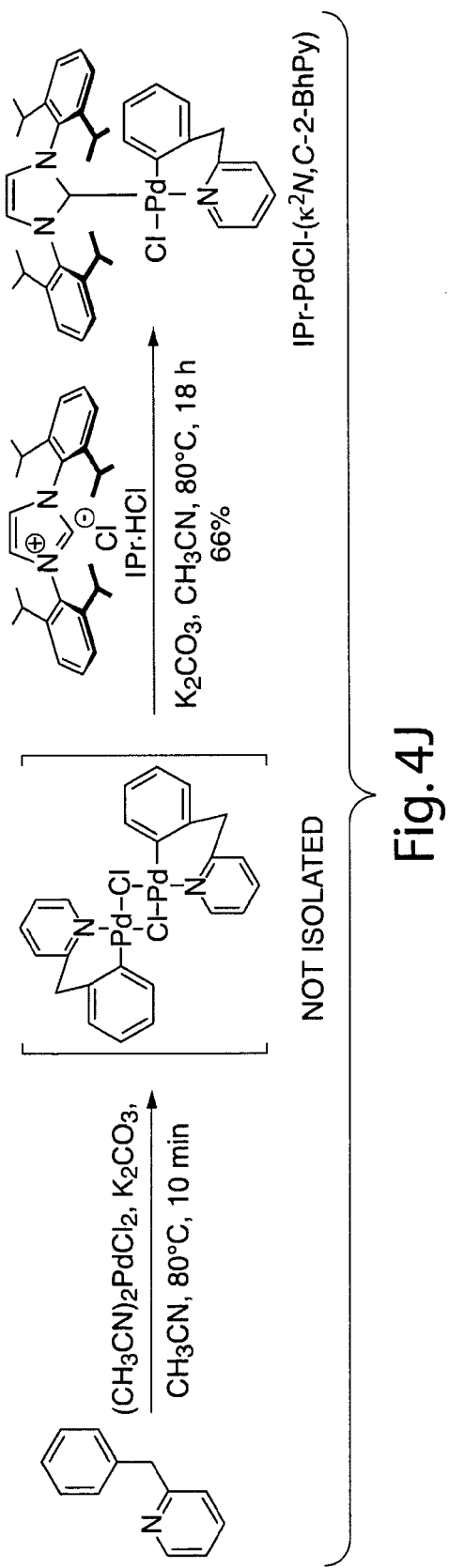

FIG. 4J shows a schematic synthesis of IPr—PdCl-[k$^2$N, C-2-PhPy], which was synthesized according to the following method. Finely powdered (CH$_3$CN)$_2$PdCl$_2$ (259 mg, 1.00 mmol) was suspended in CH$_3$CN (5 mL) and 2-benzylpyridine (170 µL, 178 mg, 1.05 mmol) was added. The solution was heated to 80° C. for 5 min and finely powdered K$_2$CO$_3$ (691 mg, 5.00 mmol) was added. The stirring was continued until palladacycle formation was complete, as indicated by the formation of a canary yellow solution (5-10 min). IPr.HCl (467 mg, 1.10 mmol) was added and the mixture was stirred at 80° C. over 18 h. The reaction mixture was filtered and evaporated. The resulting product was purified by column chromatography. Upon application of the product to a pad of silica gel (2.5×8 cm) pre-equilibrated with CH$_2$Cl$_2$, CH$_2$Cl$_2$ (100 mL) was used to elute impurities. The pure NHC-palladacycles were eluted with CH$_2$Cl$_2$-ethylacetate (1:1, vol/vol, 150 mL) and the solvents were evaporated. The products triturated with hexanes (25 mL). After drying in high vacuum, IPr—PdCl-[k$^2$N, C-2-PhPy] (464 mg, 66%) was obtained as yellow solid. $^1$H NMR (CDCl$_3$, 400 MHz) δ: 8.80 (d, J=0.8 Hz, 1H), 7.56 (broad m, 1H), 7.42 (broad m, 4H), 7.20 (s, 2H), 7.07 (d, J=7.6, 2H), 7.01 (broad m, 1H), 6.89 (t, J=6.8 Hz, 1H), 6.74-6.68 (m, 3H), 6.61 (m, 1H), 3.79-3.76 (broad m, 2H), 3.37 (broad m, 3H), 2.37 (broad m, 1H), 1.64 (broad s, 3H), 1.54 (broad s 3H), 1.30 (broad s, 3H), 1.22 (broad s, 3H), 1.00 (broad s, 3H), 0.95 (broad s, 3H), 0.42 (broad s, 3H). $^{13}$C NMR (CDCl$_3$, 100 MHz) δ: 176.1, 159.4, 153.2, 150.1, 149.6, 148.2 (broad), 147.5 (broad), 145.4 (broad), 140.2, 137.3, 136.5 (broad), 136.0 (broad), 130.0 (broad), 129.4 (broad), 125.7, 125.2 (broad), 125.0, 124.6 (broad), 124.2 (broad), 123.6 (broad), 123.0 (broad), 122.3, 121.1, 49.2, 28.9, 28.8, 26.7, 26.3, 24.0, 23.2.

Example 12

Figure 5:
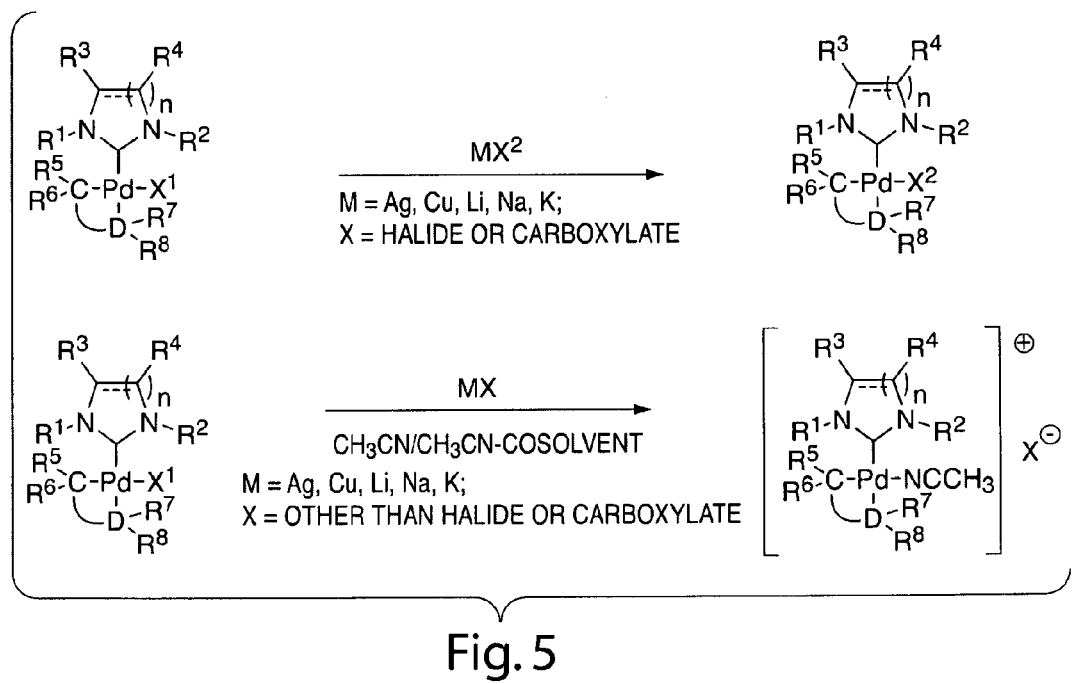
FIG. 5 shows general anion exchange reactions of precatalysts according to some embodiments of the invention.

The following example describes a general method for an anion exchange reaction for compounds of the invention, as shown in FIG. 5. FIG. 6A shows a schematic synthesis of IPr—Pd(dmba)OAc. To a suspension of AgOAc (167 mg, 1 mmol) in CH$_2$Cl$_2$ (2 mL), a solution of IPr—Pd(dmba)Cl (665 mg, 1 mmol) in CH$_2$Cl$_2$ (3 mL) was added. The mixture was stirred over 1 h and evaporated to dryness in the presence of silica gel (2 g). IPr—Pd(dmba)OAc (663 mg, 96%) was obtained as a white solid after chromatography (Combiflash, 12 g cartridge) with CH$_2$Cl$_2$-ethyl acetate:methanol (5:1, vol/vol) gradient, 0 to 100%. $^1$H NMR (CDCl$_3$, 400 MHz) δ: 7.32 (t, J=7.6 Hz, 2H), 7.22 (broad d, J=7.6 Hz, 2H), 7.12 (s, 2H), 7.10 (broad d, J=7.6 Hz, 2H), 6.68 (t, J=7.2 Hz, 2H), 6.61 (m, 3H), 6.38 (d, J=7.6 Hz, 1H), 3.24 (s, 2H), 3.20 (m, 2H), 2.81 (m, 2H), 2.18 (s, 6H), 1.40 (s, 3H), 1.33 (d, J=6.4 Hz, 6H), 1.10 (d, J=6.4 Hz, 6H), 0.93 (d, J=6.8 Hz, 6H), 0.79 (d, J=6.4 Hz, 6H). $^{13}$C NMR (CDCl$_3$, 100 MHz) δ: 178.3, 176.0, 148.2, 148.0, 147.0, 145.1, 136.0, 135.8, 129.6, 125.4, 124.2, 124.1, 123.8, 122.4, 121.7, 72.3, 49.2, 28.7, 28.5, 26.3, 25.3, 23.0, 22.8. Anal. calcd for C$_{38}$H$_{51}$N$_3$O$_2$Pd (688.25): C, 66.31; H, 7.47; N, 6.11. Found: C, 66.70; H, 7.63; N, 6.31.

Example 13

FIG. 6B shows a schematic synthesis of IPr—Pd(dmba) OCOCF$_3$. To a suspension of AgOCOCF$_3$ (221 mg, 1 mmol) in CH$_2$Cl$_2$ (2 mL), a solution of IPr—Pd(dmba)Cl (665 mg, 1 mmol) in CH$_2$Cl$_2$ (3 mL) was added. The mixture was stirred over 1 h and evaporated to dryness in the presence of silica gel (2 g). IPr—Pd(dmba)OCOCF$_3$ (733 mg, 99%) was obtained as a white solid after chromatography (Combiflash, 12 g cartridge) with CH$_2$Cl$_2$-ethyl acetate gradient, 0 to 100%. $^1$H NMR (CDCl$_3$, 400 MHz) δ: 7.42 (t, J=7.6 Hz, 2H), 7.30 (d, J=7.6 Hz, 2H), 7.25 (s, 2H), 7.21 (d, J=7.6 Hz, 2H), 6.80 (td, J=6.8, 1.2 Hz, 2H), 6.70 (m, 2H), 6.70 (d, J=7.6 Hz, 1H), 3.34 (s, 2H), 3.29 (m, 2H), 2.84 (m, 2H), 2.24 (s, 6H), 1.36 (d, J=6.8 Hz, 6H), 1.19 (d, J=6.8 Hz, 6H), 1.03 (d, J=6.8 Hz, 6H), 0.88 (d, J=6.8 Hz, 6H). $^{13}$C NMR (CDCl$_3$, 100 MHz) δ: 177.3, 160.8 (q, $^2J_{C-F}$=35 Hz), 147.6, 146.7, 145.9, 145.0, 136.0, 135.8, 135.4, 129.7, 125.7, 124.5, 124.3, 123.9, 122.7, 121.0, 160.8 116.6 (q, $^1J_{C-F}$=292 Hz), 72.0, 49.1, 28.6, 28.5, 26.3, 26.3, 23.0, 22.4. Anal. calcd for C$_{38}$H$_{48}$F$_3$N$_3$O$_2$Pd (742.22): C, 61.49; H, 6.52; N, 5.66. Found: C, 62.06; H, 6.67; N, 5.77.

Example 14

The following example describes the use of pre-catalysts of the invention in Suzuki-Miyaura cross-coupling reactions.

Figure 7A:
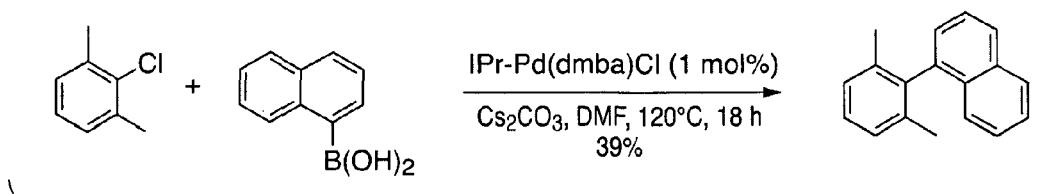
FIG. 7 shows a Suzuki-Miyaura cross-coupling between 2-chloro-1,3-xylene and 1-naphthylboronic acid using (a) a weak base and (b) a strong base, (c) a Buchwald-Hartwig amination of 2-chloro-1,3-xylene with 2,6-diisopropylaniline, and (d) a Heck-Mizoroki reaction between 4-bromo-2,6-dimethylaniline and tert-butyl acrylate.

FIG. 7A shows the schematic synthesis of the Suzuki-Miyaura cross-coupling between 2-chloro-1,3-xylene and 1-naphthylboronic acid, using a weak base. In a tube with a stirbar, 1-naphthylboronic acid (722 mg, 4.2 mmol), Cs$_2$CO$_3$ (1.95 g, 6.0 mmol) and IPr—Pd(dmba)Cl (27 mg, 0.040 mmol) were sealed with a septum and the tube was backfilled with Ar (3x). Dry DMF (12 mL) was added to the tube and the mixture was heated to 120° C. 2-Chloro-1,3-xylene (530 µL, 562 mg, 4.0 mmol) was added dropwise. The reaction was heated overnight, cooled, and partitioned between ether (20 mL) and water (20 mL). The ether layer was washed with water (4×20 mL), dried (MgSO$_4$) and evaporated. The product (359 mg, 39%) was obtained as waxy white solid after column chromatography on silica gel, using hexanes as the eluent. The $^1$H- and $^{13}$C NMR spectra were identical as described in literature (for example, as described in Navarro, O.; Kelly, R. A., III; Nolan, S. P. *J. Am. Chem. Soc.* 2003, 125, 16194-16195).

Figure 7B:
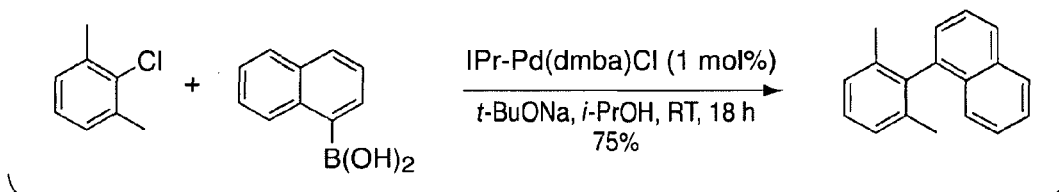

FIG. 7B shows the schematic synthesis of the Suzuki-Miyaura cross-coupling between 2-chloro-1,3-xylene and 1-naphthylboronic acid, using a strong base. In a tube with a stirbar, 1-naphthylboronic acid (1.35 g, 7.9 mmol), and t-BuONa (793 mg, 8.3 mmol) were sealed with a septum, and the tube was backfilled with Ar (3x). 2-Chloro-1,3-xylene (1.00 mL, 1.06 g, 7.5 mmol) was added. A solution containing IPr—Pd(dmba)Cl (50 mg, 0.075 mmol) in i-PrOH (reagent grade, 8 mL) was injected and the catalyst was activated by heating with heat gun. The reaction was stirred at room temperature overnight, the solvent removed and the residue partitioned between CH$_2$Cl$_2$ (30 mL) and water (50 mL). The organic layer was separated, dried (MgSO$_4$) and evaporated. As described above, the product (1.31 g, 75%) was obtained as waxy white solid after column chromatography on silica gel, using hexanes as the eluent.

Example 15

The following example describes the use of a pre-catalyst of the invention in a Buchwald-Hartwig amination reaction.

Figure 7C:
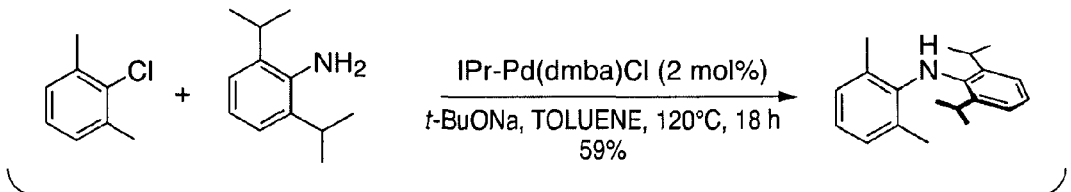

FIG. 7C shows the schematic synthesis of the Buchwald-Hartwig amination of 2-chloro-1,3-xylene with 2,6-diisopropylaniline. A vial with a stirbar was charged with t-BuONa (173 mg, 1.8 mmol). A solution containing IPr—Pd(dmba)Cl (13.3 mg, 0.020 mmol) in toluene (reagent grade; 2 mL) was added to the vial. 2-Chloro-1,3-xylene (135 μL, 141 mg, 1.0 mmol) and 2,6-diisopropylaniline (225 μL, 212 mg, 1.2 mmol) were added in succession. The atmosphere above the vial was purged with a stream of Ar, and the vial was capped, sealed, and heated at 120° C. over 18 h. The crude reaction mixture was transferred into a round-bottomed flask, and the volatile solvents were removed. The remaining residue was purified by column chromatography on silica gel (Combiflash 12 g cartridge, hexane over 5 min, then hexane-ethyl acetate 0 to 100% gradient over 15 min). The product (167 mg, 59%) was obtained as colorless oil. The $^1$H- and $^{13}$C NMR were identical as described in the literature (for example, as described in Wolfe, J. P.; Tomori, H.; Sadighi, J. P.; Yin, J.; Buchwald, S. L. *J. Org. Chem.* 2000, 65, 1158-1174).

Example 16

The following example describes the use of a pre-catalyst of the invention in a Heck-Mizoroki cross-coupling reaction.

Figure 7D:
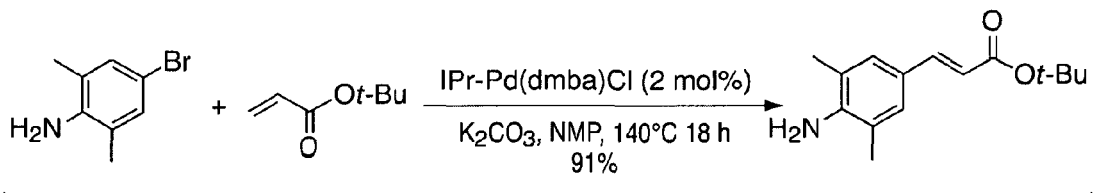

FIG. 7D shows the schematic synthesis of the Heck-Mizoroki reaction between 4-bromo-2,6-dimethylaniline and tert-butyl acrylate. A vial was charged with a stirbar, 4-bromo-2,6-dimethylaniline (200 mg, 1.0 mmol), K$_2$CO$_3$ (276 mg, 2.0 mmol) and IPr—Pd(dmba)Cl (13.3 mg, 0.020 mmol). The vial was backfilled with Ar (3×), and NMP (purged with Ar; 2 mL) and tert-butyl acrylate (175 μL, 154 mg, 1.2 mmol) were added via syringe. The mixture was heated to 140° C. overnight, cooled, and partitioned between ether (20 mL) and water (20 mL). The ether layer was washed with water (2×20 mL) and dried (MgSO$_4$), and the solvent was evaporated. The product (225 mg, 91%) was obtained as pale yellow oil after purification by column chromatography on silica gel (Combiflash 12 g cartridge, hexane-ethyl acetate 0 to 10% gradient over 20 min). $^1$H NMR (CDCl$_3$, 400 MHz) δ: 7.48 (d, J=16.0 Hz, 1H), 7.15 (s, 2H), 6.19 (d, J=16.0 Hz, 1H), 2.19 (s, 6H), 1.53 (s, 9H). $^{13}$C NMR (CDCl$_3$, 100 MHz) δ: 167.2, 145.0, 144.3, 128.6, 124.3, 121.5, 115.3, 79.8, 28.3, 17.6. Using a similar procedure (NMP, volume 0.4 mL), the product (88%, 217 mg) was obtained with IMes-Pd(dmba)Cl (11.6 mg, 0.020 mmol) as an alternative precatalyst,

DEFINITIONS

For convenience, certain terms employed in the specification, examples, and appended claims are listed here.

The term "catalytic amount" is recognized in the art and refers to a substoichiometric amount relative to a reactant.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups, all optionally substituted. In some embodiments, a straight chain or branched chain alkyl has 30 or fewer carbon atoms in its backbone (e.g., C$_1$-C$_{30}$ for straight chain, C$_3$-C$_{30}$ for branched chain), and, in some cases, 20 or fewer.

The term "heteroalkyl" refers to an alkyl group as described herein in which one or more carbon atoms is replaced by a heteroatom. Suitable heteroatoms include oxygen, sulfur, nitrogen, phosphorus, and the like. The term "cycloheteroalkyl" refers to cycloalkyl groups in which one or more carbon atoms is replaced by a heteroatom.

The term "aryl" refers to aromatic carbocyclic groups, optionally substituted, having a single ring (e.g., phenyl), multiple rings (e.g., biphenyl), or multiple condensed rings in which at least one is aromatic (e.g., 1,2,3,4-tetrahydronaphthyl, naphthyl, anthryl, or phenanthryl). That is, at least one ring may have a conjugated pi electron system. The aryl group may be optionally substituted, as described herein. "Carbocyclic aryl groups" refer to aryl groups wherein the ring atoms on the aromatic ring are carbon atoms. Carbocyclic aryl groups include monocyclic carbocyclic aryl groups and polycyclic or fused compounds such as naphthyl groups.

"Heterocyclic aryl" or "heteroaryl" groups are aryl groups wherein at least one ring atom in the aromatic ring is a heteroatom, and the remainder of the ring atoms being carbon atoms. Suitable heteroatoms include oxygen, sulfur, nitrogen, phosphorus, and the like. Suitable heteroaryl groups include furanyl, thienyl, pyridyl, pyrrolyl, N-lower alkyl pyrrolyl, pyridyl-N-oxide, pyrimidyl, pyrazinyl, imidazolyl, indolyl and the like, all optionally substituted.

The term "aralkyl" refers to an alkylene group substituted with an aryl group. Suitable aralkyl groups may include benzyl, picolyl, and the like, and may be optionally substituted. The aryl portion may have 5-14 ring atoms and the alkyl portion may have up to and including 10 carbon atoms. "Heteroarylalkyl" refers to an alkylene group substituted with a heteroaryl group.

The terms "amine" and "amino" are art-recognized and refer to both unsubstituted and substituted amines, e.g., a moiety that can be represented by the general formula: N(R') (R")(R"') wherein R', R", and R"' each independently represent a group permitted by the rules of valence.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate, p-toluenesulfonate, methanesulfonate, and nonafluorobutanesulfonate functional groups and molecules that contain said groups in either neutral (e.g., ester) form or ionic (e.g., salt) form, respectively.

The term "carbonyl" is recognized in the art and refers to the group, C=O.

The terms "carboxyl group," "carbonyl group," and "acyl group" are recognized in the art and can include such moieties as can be represented by the general formula:

wherein W is H, OH, O-alkyl, O-alkenyl, or a salt thereof. Where W is O-alkyl, the formula represents an "ester." Where W is OH, the formula represents a "carboxylic acid." The term "carboxylate" refers to an anionic carboxyl group. In general, where the oxygen atom of the above formula is replaced by sulfur, the formula represents a "thiolcarbonyl" group. Where W is a S-alkyl, the formula represents a "thiolester." Where W is SH, the formula represents a "thiolcarboxylic acid." On the other hand, where W is alkyl, the above formula represents a "ketone" group. Where W is hydrogen, the above formula represents an "aldehyde" group.

The terms "alkenyl" and "alkynyl" refer to unsaturated aliphatic groups analogous in length and possible substitution to the alkyls described above, but which contain at least one double or triple carbon-carbon bond, respectively. The term "alkenylalkyl" refers to an alkyl groups substituted with an alkenyl group. The term "alkynylalkyl" refers to an alkyl groups substituted with an alkynyl group.

The term "alkoxy-" or "alkyloxy-" refers to the group O-alkyl.

The term "halide" refers to —F, —Cl, —Br, or —I.

The term "sulfonate" is given its ordinary meaning in the art and refers to the group, $SO_3W'$, where W' may be an electron pair, hydrogen, alkyl, cycloalkyl, or aryl.

As used herein, the term "substituted" is contemplated to include all permissible substituents of organic compounds, "permissible" being in the context of the chemical rules of valence known to those of ordinary skill in the art. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted aldehyde" must still comprise the aldehyde moiety and can not be modified by substitution, in this definition, to become, e.g., a carboxylic acid. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

Examples of substituents include, but are not limited to, alkyl, aryl, aralkyl, cyclic alkyl, heterocycloalkyl, hydroxy, alkoxy, aryloxy, perhaloalkoxy, aralkoxy, heteroaryl, heteroaryloxy, heteroarylalkyl, heteroaralkoxy, azido, amino, halide, alkylthio, oxo, acylalkyl, carboxy esters, carboxyl, -carboxamido, nitro, acyloxy, aminoalkyl, alkylaminoaryl, alkylaryl, alkylaminoalkyl, alkoxyaryl, arylamino, aralkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, arylalkyloxyalkyl, and the like.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B", when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of", when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed:

1. A method for synthesizing a transition metal-containing precatalyst, comprising:
   reacting a palladium-containing compound, an N-heterocyclic carbene ligand precursor, and a compound having the structure,

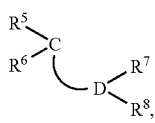

all contained together in a single reaction chamber, to form a transition metal-containing precatalyst having one of the following structures,

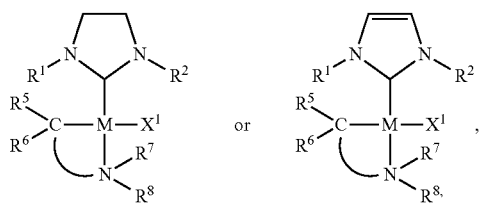

wherein:
M is Pd, Pt, or Ru;
$X^1$ is halide;
C is phenyl;
$R^1$ and $R^2$ are phenyl groups substituted with one, two, or three alkyl groups selected from the group consisting of methyl, ethyl, isopropyl, and t-butyl;
$R^5$ and $R^6$ can be the same or different and are hydrogen, t-butyl, methoxy, or trifluoromethyl;
$R^7$ and $R^8$ can be the same or different and are methyl, isopropyl, t-butyl, phenyl, phenoxy, or hydroxyl, or, one of $R^7$ and $R^8$ is methyl, isopropyl, t-butyl, phenyl, phenoxy, or hydroxyl and the other forms a bond with an atom of ⌐; ;

⌐ is alkyl or alkyl-substituted alkyl,
wherein the palladium-containing compound, the N-heterocyclic carbene ligand precursor, and the compound are not joined by a bond prior to reacting.

2. A method as in claim 1, wherein M is Pd, $R^1$ and $R^2$ are phenyl rings substituted with methyl, ethyl, isopropyl, tert-butyl or combinations thereof.

3. A method as in claim 1, wherein the transition metal-containing precatalyst has the following structure,

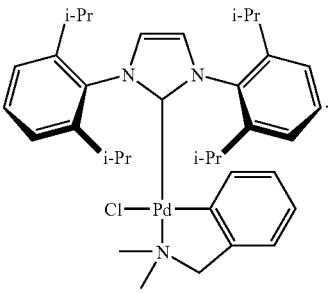

4. A method as in claim 1, wherein the transition metal-containing precatalyst has the following structure,

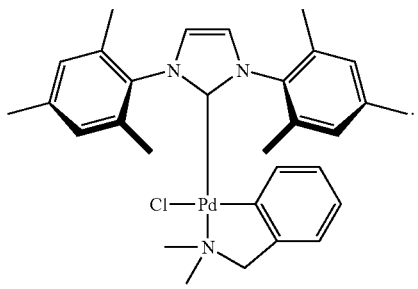

5. A method as in claim 1, wherein the transition metal-containing precatalyst is stable in the presence of oxygen.

6. A method as in claim 1, wherein the transition metal-containing precatalyst is stable in the presence of water.

7. A method as in claim 1, wherein the palladium-containing compound is $PdCl_2$.

8. A method as in claim 1, wherein the palladium-containing compound is $(CH_3CN)_2PdCl_2$.

9. A method as in claim 1, further comprising a base.

10. A method as in claim 9, wherein the base is an inorganic base.

11. A method as in claim 9, wherein the base is a carbonate, phosphate, halide, or hydride.

12. A method as in claim 9, wherein the base is potassium carbonate, cesium carbonate, sodium carbonate.

13. A method as in claim 9, wherein the base is $K_2CO_3$.

14. A method as in claim 1, further comprising a solvent.

15. A method as in claim 14, wherein the solvent is a polar solvent.

16. A method as in claim 14, wherein the solvent is acetonitrile, acetone, methanol, ethanol, propanol, butanol, ethylene glycol dimethyl ether, dimethylformamide, tetrahydrofuran, dimethylsulfoxide.

17. A method as in claim 14, wherein the solvent is a acetonitrile.

18. A method as in claim 1, further comprising an inorganic salt.

19. A composition of matter, comprising a compound having one of the following structures,

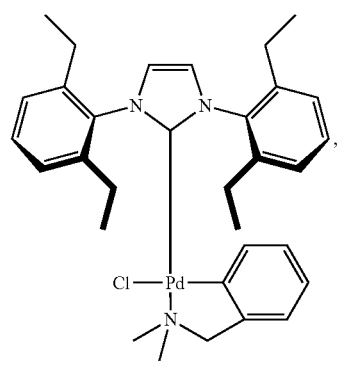

35
-continued
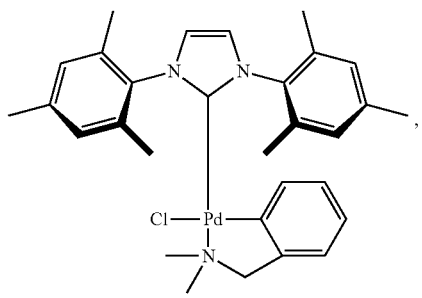
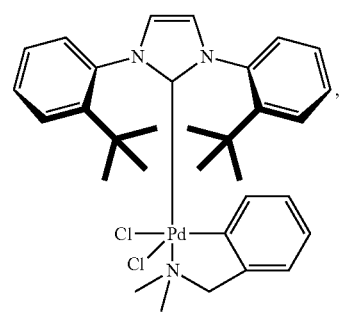
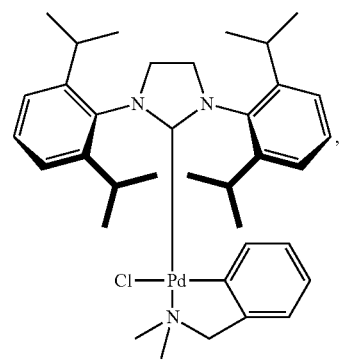
36
-continued
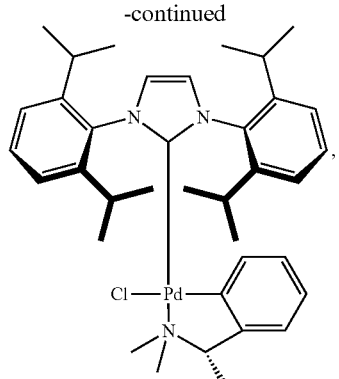
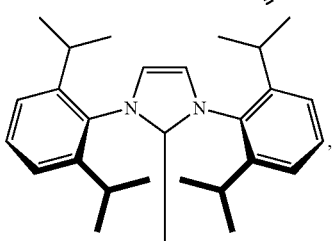
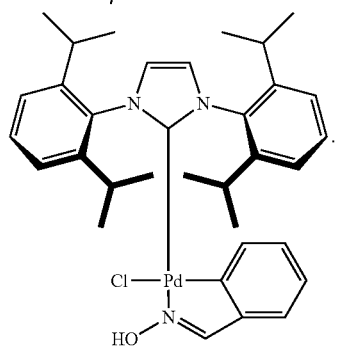
* * * * *